United States Patent
Brodie et al.

(10) Patent No.: US 10,973,857 B2
(45) Date of Patent: Apr. 13, 2021

(54) MESENCHYMAL STEM CELL AND USE THEREOF FOR TREATMENT OF MUSCLE INJURY AND MUSCLE-ASSOCIATED DISEASES

(71) Applicant: EXOSTEM BIOTEC LTD., Tel Aviv (IL)

(72) Inventors: Chaya Brodie, Southfield, MI (US); Shlomit Brodie, Nof Ayalon (IL)

(73) Assignee: EXOSTEMBIOTEC LTD., Tel Aviv (IL)

( * ) Notice: Subject to any disclaimer, the term of this patent is extended or adjusted under 35 U.S.C. 154(b) by 0 days.

(21) Appl. No.: 16/114,487

(22) Filed: Aug. 28, 2018

(65) Prior Publication Data
US 2019/0125803 A1 May 2, 2019

Related U.S. Application Data

(63) Continuation of application No. PCT/IL2017/050548, filed on May 16, 2017.

(60) Provisional application No. 62/336,858, filed on May 16, 2016.

(51) Int. Cl.
| | |
|---|---|
| *A61K 35/51* | (2015.01) |
| *A61K 35/34* | (2015.01) |
| *A61K 35/28* | (2015.01) |
| *C12N 5/0775* | (2010.01) |
| *A61P 21/00* | (2006.01) |
| *A61P 29/00* | (2006.01) |
| *C12N 15/113* | (2010.01) |

(52) U.S. Cl.
CPC .............. *A61K 35/51* (2013.01); *A61K 35/28* (2013.01); *A61K 35/34* (2013.01); *A61P 21/00* (2018.01); *A61P 29/00* (2018.01); *C12N 5/0665* (2013.01); *C12N 15/113* (2013.01); *C12N 2310/141* (2013.01); *C12N 2502/1335* (2013.01)

(58) Field of Classification Search
None
See application file for complete search history.

(56) References Cited

U.S. PATENT DOCUMENTS

| | | |
|---|---|---|
| 2013/0004466 A1 | 1/2013 | Tremblay et al. |
| 2014/0154222 A1 | 6/2014 | Offen et al. |

FOREIGN PATENT DOCUMENTS

| | | |
|---|---|---|
| WO | 2009105044 A1 | 8/2009 |
| WO | 2016057755 A1 | 4/2016 |

OTHER PUBLICATIONS

Sienkiewwicz et al. Ther Adv Neurol Disord. Jul. 2015 8(4)/ pp. 166-177.*
Joo S et al, "Myogenic-induced mesenchymal stem cells are capable of modulating the immune response by regulatory T cells", Journal of Tissue Engineering, Feb. 2014, vol. 5, pp. 1-11.
Suzuki, Masatoshi, et al. "Direct muscle delivery of GDNF with human mesenchymal stem cells improves motor neuron survival and function in a rat model of familial ALS", Molecular Therapy, Dec. 2008, vol. 16 No. 12, pp. 2002-2010.
Liu Y et al, "Flk-1+ adipose-derived mesenchymal stem cells differentiate into skeletal muscle satellite cells and ameliorate muscular dystrophy in mdx mice", Stem Cells and Development, Oct. 2007, vol. 16 No. 5, pp. 695-706.
Goudenege, S. et al, "Enhancement of Myogenic and Muscle Repair Capacities of Human Adipose-derived Stem Cells With Forced Expression of MyoD", Jun. 2009, vol. 17 No. 6, pp. 1064-10725.
Markert CD et al, "Mesenchymal stem cells: emerging therapy for Duchenne muscular dystrophy", PM&R Journal, Jun. 2009, vol. 1 No. 6, pp. 547-559.
Rajput BS et al, "Human Umbilical Cord Mesenchymal Stem Cells in the Treatment of Duchenne Muscular Dystrophy: Safety and Feasibility Study in India", Journal of Stem Cells, 2015, vol. 10 No. 2, pp. 141-156.
Li P et al, "Transplantation of human umbilical cord-derived mesenchymal stems cells for the treatment of Becker muscular dystrophy in affected pedigree members", International Journal of Molecular Medicine, 2015, vol. 35 No. 4, pp. 1051-1057.
International Search Report of PCT/IL2017/050548 Completed Aug. 22, 2017; dated Aug. 27, 2017 4 pages.
Written Opinion of PCT/IL2017/050548 completed Aug. 22, 2017; dated Aug. 27, 2017 6 pages.
Akizawa, et al: "Enhanced expression of myogenic differentiation factors and skeletal muscle proteins in human amnion-derived cells via the forced expression of MYOD1"; Brain and Development, vol. 35, No. 4, pp. 349-355, Apr. 1, 2013.
Vishnubhatla, et al: "The Development of Stem Cell-derived Exosomes as a Cell-free Regenerative Medicine"; Journal of Circulating Biomarkers; vol. 3, No. 2, pp. 1-14, Apr. 30, 2014.
Ichim, et al: Mesenchymal stem cells as anti-inflammatories: Implications for treatment of Duchenne muscular dystrophy; Cellular Immunology; vol. 260, No. 2, pp. 75-82, Jan. 1, 2010.
Park, et al: "Placental Perivascular Cells for Human Muscle Regeneration"; Stem Cells and Development; vol. 20, No. 3, pp. 451-463, Mar. 1, 2011.

(Continued)

*Primary Examiner* — Blaine Lankford
(74) *Attorney, Agent, or Firm* — The Roy Gross Law Firm, LLC; Roy Gross

(57) ABSTRACT

Isolated cells of a mixed character, possessing a mesenchymal stem cell phenotype and a muscle cell phenotype, as well as extracellular vesicles secreted from same, pharmaceutical compositions comprising same, and methods of treatment comprising administering same, are provided. Further, methods of increasing engraftment of foreign cells by co-administering same are provided.

20 Claims, 13 Drawing Sheets
(1 of 13 Drawing Sheet(s) Filed in Color)
Specification includes a Sequence Listing.

(56) References Cited

OTHER PUBLICATIONS

Kim, et al: "MYOD mediates skeletal myogenic differentiation of human amniotic fluid stem cells and regeneration of muscle injury"; Stem Cell Research & Therapy; vol. 4, No. 6, p. 147, Dec. 11, 2013.
Gang, et al: "Engraftment of mesenchymal stem cells into dystrophin-deficient mice is not accompanied by functional recovery"; Experimental Cell Research; vol. 315, No. 15, pp. 2624-2636, Sep. 10, 2009.
Bana, et al: "A Comparative Study to Evaluate Myogenic Differentiation Potential of Human Chorion versus Umbilical Cord Blood-derived Mesenchymal Stem Cells"; Tissue and Cell; vol. 49, No. 4, pp. 495-502, May 11, 2017.

* cited by examiner

MESENCHYMAL STEM CELL AND USE THEREOF FOR TREATMENT OF MUSCLE INJURY AND MUSCLE-ASSOCIATED DISEASES

CROSS REFERENCE TO RELATED APPLICATIONS

This application is a Track One Continuation of PCT Patent Application No. PCT/IL2017/050548 having International filing date of May 16, 2017, which claims the benefit of priority of U.S. Provisional Patent Application No. 62/336,858, filed May 16, 2016. The contents of the above applications are all incorporated by reference as if fully set forth herein in their entirety.

FIELD OF INVENTION

The present invention is in the field of differentiation of mesenchymal stem cells (MSCs) to muscles, and the treatment of muscle and motor neuron disease.

BACKGROUND OF THE INVENTION

Mesenchymal stem cells (MSCs) are a heterogeneous population of mesoderm-derived stromal cells that can be obtained from autologous bone marrow, dental pulp, or adipose tissues or from allogeneic amniotic fluid, placenta and umbilical cord. As MSCs from these last three sources are non-immunogenic, they can be used as off-the-shelf cells. Recent reports have demonstrated that in addition to their natural ability to differentiate to cartilage, bone and fat cells, these cells have also the potential to be trans-differentiated into other cell types, including hepatocytes, muscle, endothelial, neuronal, and insulin-producing cells.

MSCs have been shown to exert therapeutic effects in a variety of diseases and dysfunctions in experimental animal models and more recently in pilot clinical trials (Gao et al., 2015, International Journal of Cardiology, 168: 3191-3199; Zhang et al., 2013, Journal of neuroinflammation, 10:106). These cells have the capacity to migrate to and engraft in sites of inflammation and injury and to exert local effects in the resident tissues. It has been reported that the adult MSCs are non-immunogenic, which indicates that no immunosuppression is required for their transplantation into an allogeneic host.

Studies have shown that MSCs have immunosuppressive and immunoregulatory properties. The beneficial effects of MSCs have been mainly attributed to this immunomodulatory activity and the secretion of trophic factors. Indeed, MSCs secrete a large variety of bioactive molecules, such as growth factors, cytokines and chemokines and can provide trophic support to multiple tissues. In addition, recent studies demonstrated that MSCs secrete extracellular vesicles that deliver RNA and DNA molecules in addition to various proteins as a part of intercellular communication.

Recent studies demonstrated that MSCs can also differentiate to muscle cells and that the myogenic differentiation of these cells increase their therapeutic effects in both canine and mouse Deschene's Muscular Dystrophy (DMD) animal models (Liu et al., 2007, Stem Cells and Development, 16(5):695-706; Goudenege et al., 2009, Molecular Therapy, 17(6):1064-72). Therefore, the use of MSC-derived satellite cells (SC), the main cells involved in muscle regeneration, or muscle cells themselves, has a great potential as an easily accessible source of autologous or allogeneic cells for cell replacement therapy in various muscle degenerative disorders including DMD, muscle injury, cachexia and aging in addition to motor and peripheral neuron disease.

Further, treatment with myoblasts, can be also employed for the treatment of ischemic limb injury and in diseases of motor neurons injury and degeneration. Motor neurons diseases (MNDs) are a group of progressive neurological disorders in which a degeneration and death of motor neurons occur. Like muscle diseases, these diseases are characterized by gradual muscle weakening and wasting, uncontrolled twitching and eventually loss of control of voluntary movement. Motor neurons are dependent for their survival on target-derived factors that are secreted by the innervated skeletal muscle. Therefore, administration of myoblasts provides a physiological approach to support the survival of damaged, injured or degenerated motor neurons.

Muscular dystrophies, and muscle and motor neuron disorders in general, are very difficult to treat, as genetic disorders affect all muscles/motor neurons in the body. Additionally, skeletal muscle is composed of large multi-nucleated fibers with post mitotic nuclei, thus any treatment would require the targeting of millions of cells. However, previous studies as well as our current technologies demonstrate that MSCs can decrease inflammatory responses, increase angiogenesis and abrogate fibrosis, can enhance the proliferation of SCs and can be induced to differentiate into myoblasts and SCs. In this way MSC treatments can theoretically target various disorders and condition associated with degenerative inflammatory disorders, injuries, cachexia and aging in a complementary way that affects both the tissues via paracrine effects and by replacement therapy using differentiated cells.

SUMMARY OF THE INVENTION

The present invention provides isolated cells of mixed character, exosomes secreted by same, pharmaceutical compositions comprising same, and methods of treating muscle-associated diseases and damage comprising administering those cells, exosomes or compositions. The present invention further provides methods of increasing engraftment of foreign cells, comprising co-administering with those cells the compositions of the invention.

According to a first aspect, there is provided an isolated cell of mixed character, wherein the cell displays a mesenchymal stem cell (MSC) phenotype and a muscle cell phenotype.

According to some embodiments, the MSC phenotype comprises a plurality of expression markers selected from the group consisting of: CD73, CD105, CD90, CD146, and CD44 expression and absence of WWII expression. According to some embodiments, the MSC phenotype comprises immunosuppression ability. According to some embodiments, the MSC phenotype comprises anti-inflammation ability. According to some embodiments, the MSC phenotype comprises the ability to home to sites of inflammation, injury or disease.

According to some embodiments, the muscle cell phenotype comprises a plurality of expression markers selected from the group consisting of: MyoD, Myf6, Myf5, MRF4, ITGA7, osteoprotegerin, Irisin, dystrophin, Myosin heavy chain, myogenin, PAX7, TALNEC2, C-MET, G-CSF, osteoprotegerin, IL-10, and MEF2A expression and absence of osteocalacin, PPARG3, and COL2A1 expression. According to some embodiments, the muscle cell phenotype comprises the ability to merge with a muscle syncytium. According to some embodiments, the muscle cell phenotype comprises a satellite cell phenotype. According to some embodiments, the muscle cell phenotype comprises a myoblast phenotype.

According to some embodiments, the cell is produced by: a) providing an MSC; b) contacting the MSC with at least one of: a ROCK inhibitor, an acidic medium, and 5-AZA; and c) introducing into the MSC at least one of: PDGFBB, HGF, PDGFβ PDGFAA, EGF, VEGF, TGFβ, and IGF1.

According to some embodiments, the cell is produced by further introducing into the MSC PCAT1 and NEAT1 or GAS5 and an inhibitor of PTENP1 expression.

According to some embodiments, the cell is produced by co-culturing an MSC with a muscle cell, conditioned media from a muscle cell, or an extracellular vesicle of a muscle cell.

According to some embodiments, the cell is produced by introducing into an MSC any one of NANOG, SOX2, KLF4, OCT4 or a combination thereof. According to some embodiments, the cell is produced by further incubating the MSC in a medium containing 5-AZA.

According to some embodiments, the cell is produced by culturing an MSC in any one of: an acidic medium; hypoxia; a low adherence plate; media with low serum, supplemented with FGF or EGF; media supplemented with 5-AZA; medium containing a small molecule selected from the group consisting of: a ROCK inhibitor, STAT3, an NF-KB activator, CHIR99021, metformin, tranylcypromine, a Gsk3 inhibitor, 3-deazaneplanocin A, an mTor inhibitor, a TGFβ inhibitor, Thiazovivin, A83-01, LiCl, SB431542, 5-AZA, rapamycin, ERK activators and valporic acid; and a combination thereof.

According to some embodiments, the cell is produced by introducing into an MSC at least one transcription factor selected from the group consisting of: MYF5, PAX3, PAX7, dystrophin, microdystrophin, utrophin, MyoD and PAX3, MyoD and PAX7, and MyoD and MYF5.

According to some embodiments, the cell is produced by: a) providing an MSC; b) contacting the MSC with at least one of: an acidic medium, a ROCK inhibitor, and 5-AZA; and c) introducing into the MSC at least one long noncoding RNA (lncRNA) selected from the group consisting of: BIL, PAR5, BIC, DISC2, GAS5DLG2AS, 7SK, Y1, LINCRNA, PCAT-1 SFMBT2, Y4, SCAB, MALAT1, MEG3, NEAT1, EGO, GAS5, KRASP1, LOC28519, BC200, and H19. According to some embodiments, the at least one lncRNA is selected from PAR5, DISC2 and PCAT1.

According to some embodiments, the cell is produced by further introducing into the MSC at least one lncRNA selected from the group consisting of MALAT1, MEG3, NEAT1, EGO, GAS5, KRASP1, LOC28519, BC200, and H19. According to some embodiments, the cell is produced by further down regulating in said MSC expression of at least one of ANRIL, PTENP1 and aHIF. According to some embodiments, the cell displays a satellite cell phenotype.

According to some embodiments, the cell is produced by: a) providing an MSC; b) contacting said MSC with at least one of: an acidic medium, a ROCK inhibitor, and 5-AZA; and c) introducing into said MSC at least one miRNA selected from the group consisting of: miR-10b, miR-22, miR-122, miR-125a, miR-140-5p, miR-143, miR-145, miR-146a, miR-148b, miR-150, miR-155, miR-181b, miR-215, miR-296, miR-330, miR-370, miR-429, miR-520, miR-524, miR-543, miR-550, miR-561, miR-564, miR-582, miR-583, miR-587, miR-613, miR-614, miR-629, miR-634, miR-645, miR-646, miR-649, miR-661, miR-662, miR-663, miR-665, miR-668, miR-671, miR-887, miR-1183, miR-1224, miR-1225, miR-1228, miR-1234, miR-1246, miR-1247, miR-1257, miR-1258, miR-1268, miR-1269, miR-1289, miR-1287, miR-1909, miR-1911, miR-759, miR-3150, miR-3174, miR-3180, miR-3191, miR-3197, miR-4292, miR-2115, miR-4312, miR-92, 93 and miR-99.

According to some embodiments, the at least one miR is selected from the group consisting of: miR-10b, miR-138, miR-154, miR-155, miR-181, miR-215, miR-614, and miR-668.

According to some embodiments, the MSC is derived from umbilical cord or placenta.

According to some embodiments, the cell expresses a plurality of stemness markers selected from the group consisting of: SOX2, KLF4, OCT4 and NANOG.

According to some embodiments, the cell secretes at least one trophic factor selected from: VEGF, GDNF and IGF1.

According to some embodiments, the cell comprises a muscle cell targeting moiety on the cell's surface or a surface of the cell's extracellular vesicles. According to some embodiments, the muscle cell targeting moiety comprises any one of: a ligand to caveolin3, M-cadherin, a ligand to the nicotinic acetylcholine receptor, a mutant dominant negative form of myostatin, and angiotensin II type 1. According to some embodiments, the muscle cell targeting moiety comprises M-cadherin.

According to some embodiments, the cell comprises a therapeutic agent. According to some embodiments, the therapeutic agent is selected from the group consisting of: a drug, a read-through drug, an RNA, a DNA molecule, a vector, an exon skipping oligonucleotide, a microRNA (miR), a small interfering RNA (siRNA) an antagomir, a long noncoding RNA (lncRNA) and a virus. According to some embodiments, the RNA is a modified MyoD mRNA. According to some embodiments, the antagomir is selected from the group consisting of: anti-miR-424, anti-miR-195, anti-miR-16, anti-miR-497, anti-miR-135, anti-miR-6793, anti-miR-21, miR-133b and a combination thereof. According to some embodiments, the antagomir is anti-let-7.

According to another aspect, there is provided isolated extracellular vesicles of any of the cells of the invention.

According to another aspect, there is provided a pharmaceutical composition comprising any one of: a cell of mixed character of the invention, an extracellular vesicle of the invention, and a combination thereof.

According to some embodiments, the pharmaceutical compositions of the invention, further comprise a pharmaceutically acceptable carrier or adjuvant.

According to another aspect, there is provided a method of treating, preventing or ameliorating a muscle-associated disease or muscle damage in a subject in need thereof, the method comprising administering a pharmaceutical composition of the invention to the subject, thereby treating, preventing or ameliorating the muscle-associated disease or damage.

According to some embodiments, the composition comprises a cell derived from an MSC that is allogenic or autologous to the subject.

According to some embodiments, the muscle-associated disease or muscle damage is selected from the group consisting of: a motor neuron disease, a peripheral neuron disease, a muscular dystrophy, spinal cord injury, muscle wasting, cardiac muscle injury, inflammatory myopathy, myasthenia gravis, sarcopenia, cachexia, and skeletal muscle injury. According to some embodiments, the muscle-associated disease is selected from the group consisting of: amyotrophic lateral sclerosis (ALS), cachexia, and a muscular dystrophy. According to some embodiments, the muscular dystrophy is Duchene's muscular dystrophy (DMD).

According to some embodiments, the muscle-associated disease is ALS and the method further comprises administering at least one MSC differentiated toward an astrocyte phenotype or a neuronal stem cell (NSC) phenotype.

According to some embodiments, the methods of the invention, further comprise administering any one of: an undifferentiated MSC, the extracellular vesicles of the undifferentiated MSC, and a combination thereof.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1B) A bar chart showing relative expression levels of TNFα, Utrophin, Collagen I and NCAM in the quadricep muscle of MDX mice 4 weeks after injection of $5\times10^5$ MSCs or their exosomes. (FIG. 1C) A bar chart showing relative expression levels of Utrophin in the quadricep muscle of MDX mice 4 weeks after injection of $5\times10^5$ MSCs from various tissues. (FIG. 1D) A bar chart showing relative expression levels of Collagen I in the quadricep muscle of MDX mice 4 weeks after injection of $5\times10^5$ MSCs from various tissues. (FIG. 1E) A bar chart showing percent regeneration, as measured by counting NCAM positive cells in quadriceps of mdx mice 4-weeks after injection of exosomes from $5\times10^5$ MSCs. (FIG. 1F) A bar chart showing relative levels of utrophin expression in human muscle cells cocultured with MSCs from various tissues. (FIG. 1G) A bar chart showing the % of myoblasts that had formed into myotubes of at least 4 cells, and (FIG. 1H) a western blot image showing MYH2 protein expression, in healthy myoblasts after coculture with MSCs of various tissues. (FIG. 1I) A bar chart showing the % of myoblasts that had formed into myotubes of at least 4 cells in myoblasts from DMD patients after coculture with MSCs of various tissues. (FIG. 1J) A western blot image of MyoD protein expression in satellite cells after coculture with MSC of various tissues or their exosomes. (FIG. 1K) A western blot image of MyoD protein expression in mouse C2C12 cells after coculture with MSC of various tissues or their exosomes. BM-bone marrow, AD-adipose, AM-amniotic placenta, CH-chorionic placenta, UC-umbilical cord.

(FIG. 4B) A bar chart showing the number of newly generated muscle fibers in the gastrocnemius muscle of wild-type mice 7 days after cardiotoxin treatment. Mice were preinjected with either PBS, MSCs or primed MSCs.

(FIG. 5B) A bar chart showing relative expression levels of MyoD, Dystrophin and Myogenin in MSCs derived from various tissues after treatment with Protocol 1 to differentiate them to hybrid cells. (FIG. 5C) A micrograph showing hybrid cells (labeled in red) and muscle cells (labeled in green) grown together. Locations of fusion between muscle cells and hybrid cells appear as yellow (arrows). (FIG. 5D) A bar chart showing relative expression levels of MyoD, Dystrophin and Myogenin in MSCs derived from various tissues after treatment with Protocol 2 to differentiate them to hybrid cells. (FIG. 5E) A bar chart showing relative expression levels of GDNF, IGF1 and VEGF in MSCs derived from various tissues after treatment with Protocol 1 to differentiate them to hybrid cells. (FIG. 5F) A bar chart showing relative MyoD expression in MSCs primed with Nanog mRNA or a control mRNA and then differentiated to hybrid cells with Protocol 3. (FIG. 5G) A bar chart showing relative levels of cells with a satellite cell phenotype, as measured by cells that are double positive for Pax7 and MyoD after differentiation with Protocol 5 with the listed lncRNAs. (FIG. 5H) A micrograph showing the morphology of control untreated MSCs and hybrid cells produced with Protocol 5 and downregulation of ANRIL, PTENP1 and aHIF. (FIG. 5I) A bar chart showing relative numbers of MyoD positive cells after priming with acidic media and hypoxia or priming with 5-AZA and differentiation with Protocol 6 using the listed miRs.

(FIG. 6B) A bar chart showing creatine kinase (CPK) levels in MDX mice quadriceps muscles 3 weeks after injection with PBS and unmodified MSCs from various tissues. (FIG. 6C) A bar chart showing creatine kinase (CPK) levels in MDX mice quadriceps muscles 3 weeks after injection with PBS and hybrid cells derived from various tissues. (FIG. 6D) A bar chart showing relative human dystrophin mRNA expression in mdx mice quadriceps muscles 3 weeks after injection with control untreated CH-MSCs, CH-MSCs primed with acidic media and hypoxia, CH-MSCs primed with muscle coculture, and hybrid cells produced with Protocol 3. (FIG. 6E) A bar chart showing creatine kinase (CPK) levels in mdx mice quadriceps muscles 3 weeks after injection with exosomes from unmodified MSCs, exosomes from hybrid cells a mix of the two, and PBS.

(FIG. 7B) A Kaplan-Meier survival plot of pre-symptomatic SOD rats injected intrathecally with PBS or MSCs differentiated to an astrocyte phenotype (MSC-AS). Rats were sacrificed when no longer able to regain their upright position within 30 seconds after being placed on their backs. (FIG. 7C) A bar chart showing the survival period (in days) of symptomatic SOD rats injected intrathecally with MSC-AS, intramuscularly with hybrid cells, with both or with PBS. Rats were sacrificed when no longer able to regain their upright position within 30 seconds after being placed on their backs. (FIG. 7D) A Kaplan-Meier survival plot of pre-symptomatic SOD rats injected intramuscularly with PBS or hybrid cells. Rats were sacrificed when no longer able to stand on a Rotarod for 10 minutes. (FIG. 7E) A Kaplan-Meier survival plot of pre-symptomatic SOD rats injected intravenously with PBS or MSCs differentiated to a neuronal stem cell phenotype (MSC-NSC). Rats were sacrificed when no longer able to stand on a Rotarod for 10 minutes.

(FIG. 9B) A western blot image showing utrophin expression in muscle cells in vivo after injection of CH-MSCs expressing antagomirs to let-7 and miR-133b. (FIG. 9C) A western blot image showing utrophin expression in muscle cells in vivo after injection of muscle-targeted and untargeted exosomes from CH-MSCs expressing an antagomir to let-7. (FIG. 9D) A bar chart showing the relative number of myosin heavy chain positive cells after coculture with CH-MSCs expressing an antagomir to let-7. (FIG. 9E) A bar chart showing the number of myoblast cells showing nuclear staining for MyoD protein following introduction into the cells of a modified MyoD mRNA by transfection, incubation with preloaded exosomes from MSCs, or trans-well coculture with MSC expressing the modified mRNA.

DETAILED DESCRIPTION OF THE INVENTION

Figure 1A:
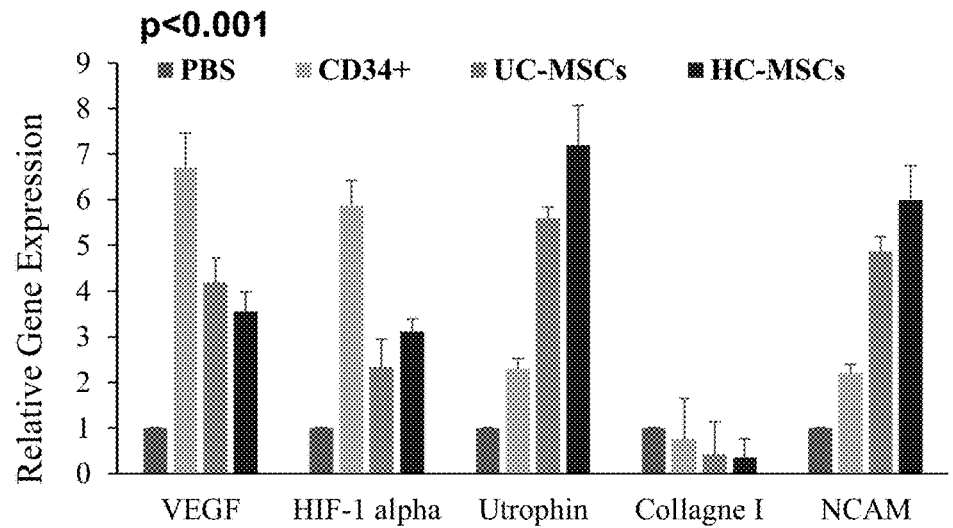
FIGS. 1A-1K. MSCs increase regeneration and decrease fibrosis (FIG. 1A) A bar chart showing relative expression levels of VEGF, HIF1α, Utrophin, Collagen I and NCAM in the quadricep muscle of wild-type mice 4 weeks after injection of $5\times10^5$ MSCs or CD34$^+$ cells.

The present invention provides cells with a mesenchymal stem cell phenotype and a muscle cell phenotype, as well as extracellular vesicles secreted from same, pharmaceutical compositions comprising same, and methods of treatment comprising administering same.

Cells of Mixed Character

By one aspect, the present invention concerns an isolated cell of mixed character, wherein the cell displays a mesenchymal stem cell (MSC) phenotype and a muscle cell phenotype.

As used herein, the term "mesenchymal stem cell" or "MSC", refers to multipotent stromal stem cells that have the ability to differentiate into osteoblasts, adipocytes, myocytes, chondroblasts, skeletal muscle cells and endothelial cells. MSC are present in the bone marrow, adipose tissue, peripheral blood, chorionic placenta, amniotic placenta, umbilical cord blood, and dental pulp, among other tissues. The term "multipotent" refers to stem cells which are capable of giving rise to many cell types.

In some embodiments, the cell is a mammalian cell. In some embodiments, the cell is a human cell. In some embodiments, the cell is an animal cell such as of a veterinary animal. In some embodiments, the veterinary animal is selected from, a cat, a dog, a horse, a cow, a pig, a sheep and a goat. In some embodiments, the cell is allogenic to a subject in need of treatment for a muscle-associated disease or muscle injury. In some embodiments, the cell is autologous to a subject in need of treatment for a muscle disease or a muscle injury.

In some embodiments, the cell of mixed character is a primed cell. As used herein, "primed cell" refers to a cell that has begun the process of differentiation toward a muscle cell, but is very early in the process. Such a cell expresses MyoD. In some embodiments, a muscle cell is a smooth muscle cell, a skeletal muscle cell or a satellite cell.

In some embodiments, a primed cell is a de-differentiated MSC. In some embodiments, a de-differentiated MSC expresses at least one of SOX2, NANOG, OCT4 and KLF4. In some embodiments, a de-differentiated MSC expresses at least one of SOX2, NANOG, OCT4 and KLF4 at a level higher than it is expressed in an untreated MSC. In some embodiments, a de-differentiated MSC expresses a plurality of SOX2, NANOG, OCT4 and KLF4. In some embodiments, a de-differentiated MSC does not differentiate or differentiates poorly into bone, adipose or tendon. In some embodiments, a de-differentiated MSC differentiates into bone adipose or tendon at a worse rate than does an untreated MSC. In some embodiments, a de-differentiated MSC differentiates to bone, adipose or tendon at less than 0.5, 0.4, 0.3, 0.2, 0.1, 0.05, or 0.01 the rate than an untreated MSC differentiates. Each possibility represents a separate embodiment of the invention.

In some embodiments, the cell of mixed character is a hybrid cell. As used herein, "hybrid cell" refers to a cell having qualities, characteristics, expression profiles or phenotypes of two different and distinct cell types, for example an MSC and a muscle cell. It does not refer to a physical hybrid in which two separate cells have been made to fuse together. As used here, a hybrid cell is an MSC differentiated toward a muscle cell that has not completed differentiation. In some embodiments, a hybrid cell is further differentiated toward a muscle cell than is a primed cell.

In some embodiments, an MSC phenotype comprises expression of at least one surface marker selected from the group consisting of: CD73, CD105, CD90, CD44 and CD146. In some embodiments, an MSC phenotype comprises expression of a plurality of surface markers selected from the group consisting of: CD73, CD105, CD90, CD44 and CD146. In some embodiments, an MSC phenotype comprises expression of IL-10. In some embodiments, an MSC phenotype comprises absence of Major Histocompatibility Complex protein II (MHCII) expression. In some embodiments, an MSC phenotype comprises at least one expression marker selected from the group consisting of: CD73, CD105, CD90, CD146, and CD44 expression and absence of MHCII expression. In some embodiments, an MSC phenotype comprises a plurality of expression markers selected from the group consisting of: CD73, CD105, CD90, CD146, and CD44 expression and absence of MHCII expression.

The term "expression" as used herein refers to the biosynthesis of a gene product, including the transcription and/or translation of said gene product. Thus, expression of a nucleic acid molecule may refer to transcription of the nucleic acid fragment (e.g., transcription resulting in mRNA or other functional RNA) and/or translation of RNA into a precursor or mature protein (polypeptide). In some embodiments, expression markers refer to RNA expression. In some embodiments, expression markers refer to protein expression. In some embodiments, surface expression markers refer to expression of proteins on the cell surface or in the plasma membrane of a cell.

In some embodiments, an MSC phenotype comprises anti-inflammation ability. In some embodiments, the MSC described herein is an anti-inflammatory cell. In some embodiments, an MSC phenotype comprises the ability to decrease inflammation. In some embodiments, an MSC phenotype comprises secretion of anti-inflammatory cytokines. Anti-inflammatory cytokines are well known to one of skill in the art, and include, but are not limited to, IL-10, IL-4, IL-13, and transforming growth factor beta (TGFβ).

In some embodiments, an MSC phenotype comprises the ability to home to sites of inflammation, injury or disease.

In some embodiments, an MSC phenotype comprises immunomodulation ability. In some embodiments, an MSC phenotype comprises the ability to modulate a subject's immune system. In some embodiments, an MSC phenotype comprises immunosuppression ability. In some embodiments, an MSC phenotype comprises the ability to suppress a subject's immune system. In some embodiments, an MSC phenotype comprises the ability to decrease activation of T-cells.

In some embodiments, an MSC phenotype comprises the ability to home to sites of inflammation, injury or disease.

Methods of detecting and determining an MSC phenotype are known to one skilled in the art. They include, but are not limited to, staining for MSC surface markers by assays such as FACS or Western Blot. Several commercial kits are available for performing this detecting and determining, including the Human and the Mouse Mesenchymal Stem Cell ID Kits (R&D Systems), MSC Phenotyping Kit, human (Miltenyi Biotech) and the BD Stemflow hMSC Analysis Kit (BD Biosciences). Other methods include measuring secreted pro- and anti-inflammatory cytokines, such as but not limited to IL-1, IL-2, IL-4, IL-10, TNFα, IL-13, and TGFβ, measuring cell homing using homing assays well known in the art and detecting and measuring mRNA expression of MSC transcription factor.

In some embodiments, a muscle cell phenotype comprises expression of at least one of: MyoD, Myf6, Myf5, MRF4, ITGA7, GFF11, osteoprotegerin, Irisin, dystrophin, Myosin heavy chain, myogenin, PAX7, TALNEC2, C-MET, G-CSF, osteoprotegerin, IL-10, and MEF2A. In some embodiments, a muscle cell phenotype comprises expression of a plurality of MyoD, Myf6, Myf5, MRF4, ITGA7, osteoprotegerin, Irisin, dystrophin, Myosin heavy chain, myogenin, PAX7, TALNEC2, C-MET, G-CSF, osteoprotegerin, IL-10, and MEF2A. In some embodiments, a muscle cell phenotype comprises at least one expression marker selected from the group consisting of: MyoD, Myf6, Myf5, MRF4, ITGA7, osteoprotegerin, Irisin, dystrophin, Myosin heavy chain, myogenin, PAX7, TALNEC2, C-MET, G-CSF, osteoprotegerin, IL-10, and MEF2A expression and absence of osteocalcin, PPARG3, and COL2A1 expression. In some embodiments, a muscle cell phenotype comprises a plurality of expression markers selected from the group consisting of: MyoD, Myf6, Myf5, MRF4, ITGA7, osteoprotegerin, Irisin, dystrophin, Myosin heavy chain, myogenin, PAX7, TALNEC2, C-MET, G-CSF, osteoprotegerin, IL-10, and MEF2A expression and absence of osteocalcin, PPARG3, and COL2A1 expression.

In some embodiments, the above described muscle expression markers are expressed at a level higher than they are expressed in undifferentiated MSCs. In some embodiments, they are expressed at a level at least 2, 3, 4, 5, 6, 7, 8, 9, or 10 times higher than they are expressed in undifferentiated MSCs. Each possibility represents a separate embodiment of the invention.

In some embodiments, a muscle cell phenotype comprises the ability to merge with a muscle syncytium. In some embodiments, a muscle cell phenotype comprises the ability to increase the size or diameter of a myotube. In some embodiments, a muscle cell phenotype is muscle regeneration. In some embodiments, a muscle cell phenotype is the ability to regenerate muscle tissue after injury or damage. In some embodiments, a muscle cell phenotype is the ability to generate new muscle fibers.

In some embodiments, a muscle cell phenotype is a satellite cell phenotype. In some embodiments, a muscle cell phenotype is a smooth muscle phenotype. In some embodiments, a muscle cell phenotype is a skeletal muscle phenotype. In some embodiments, a muscle cell phenotype is a cardiac muscle phenotype.

Methods of detecting and determining a muscle cell phenotype are known to one skilled in the art. They include, but are not limited to, staining for muscle proteins, for example by Western blot, FACS or ELISA; quantitative PCR to detect and quantify muscle cell transcription factor and proteins; and assaying for fusion to a muscle syncytium. Assays for muscle fusion are well known in the art and may employ double fluorescent tags to look for a mix of colors.

Production of Cells

Protocol A: In some embodiments, the cell of the invention is produced by co-culturing an MSC with a muscle cell, conditioned media from a muscle cell, or an extracellular vesicle of a muscle cell.

Protocol B: In some embodiments, the cell of the invention is produced by introducing into an MSC any one of NANOG, SOX2, KLF4, OCT4 or a combination thereof. In some embodiments, the cell of the invention is produced by introducing Nanog into an MSC.

Protocol C: In some embodiments, the cell of the invention is produced by incubating an MSC with 5-azacytidine (5-AZA).

Protocol D: In some embodiments, the cell of the invention is produced by incubating an MSC with a) a ROCK inhibitor and b) acidic media or hypoxia.

Protocol E: In some embodiments, the cell of the invention is produced by culturing an MSC in any one of: an acidic medium; hypoxia; a low adherence plate; media with low serum, supplemented with FGF or EGF; medium containing a small molecule selected from the group consisting of: a ROCK inhibitor, a STAT3 activator, an NF-KB activator, CHIR99021, metformin, tranylcypromine, a Gsk3 inhibitor, 3-deazaneplanocin A, an mTor inhibitor, a TGFβ inhibitor, Thiazovivin, A83-01, LiCl, SB431542, 5-AZA, rapamycin, ERK activators and valporic acid; and a combination thereof.

Protocol 1: In some embodiments, a cell of the invention can be produced by providing an MSC, contacting the MSC with at least one of an acidic medium, a ROCK inhibitor, and 5-AZA, introducing into the MSC HGF or PDGFβ, and introducing into the MSC PCAT1 and NEAT1.

Protocol 2: In some embodiments, a cell of the invention can be produced by providing an MSC, contacting the MSC with at least one of an acidic medium, a ROCK inhibitor, and 5-AZA, introducing in the MSC HGF or PDGFβ, and introducing into the MSC GAS5 and an inhibitor of PTENP1 expression.

Protocol 3: In some embodiments, a cell of the invention is produced by providing an MSC; contacting the MSC with at least one of: an acidic medium, a ROCK inhibitor, and 5-AZA, and introducing into the MSC at least one growth factor selected from the group comprising: PDGFAA, PDGFBB, EGF, VEGF, TGFβ, and IGF1.

Protocol 4: In some embodiments, a cell of the invention is produced by introducing into an MSC at least one transcription factor selected from the group consisting of: MYF5, PAX3, PAX7, dystrophin, microdystrophin, utrophin, MyoD and PAX3, MyoD and PAX7, and MyoD and MYF5.

Protocol 5: In some embodiments, a cell of the invention is produced by providing an MSC; contacting the MSC with at least one of an acidic medium, a ROCK inhibitor, and 5-AZA; and introducing into the MSC at least one long non-coding RNA (lncRNA) selected from the group consisting of: BIL, PAR5, BIC, DISC2, GAS5DLG2AS, 7SK, Y1, LINCRNA, PCAT-1 SFMBT2, Y4, SCA8, MALAT1, MEG3, NEAT1, EGO, GAS5, KRASP1, LOC28519, BC200, and H19. In some embodiments, the at least one lncRNA is selected from PAR5, DISC2 and PCAT1.

Protocol 6: In some embodiments, a cell of the invention is produced by providing an MSC; contacting the MSC with at least one of an acidic medium, a ROCK inhibitor, and 5-AZA; and introducing into the MSC at least one miRNA (miR) selected from the group consisting of: miR-10b, miR-22, miR-122, miR-125a, miR-140-5p, miR-143, miR-145, miR-146a, miR-148b, miR-150, miR-155, miR-181b, miR-215, miR-296, miR-330, miR-370, miR-429, miR-520, miR-524, miR-543, miR-550, miR-561, miR-564, miR-582, miR-583, miR-587, miR-613, miR-614, miR-629, miR-634, miR-645, miR-646, miR-649, miR-661, miR-662, miR-663, miR-665, miR-668, miR-671, miR-887, miR-1183, miR-1224, miR-1225, miR-1228, miR-1234, miR-1246, miR-1247, miR-1257, miR-1258, miR-1268, miR-1269, miR-1289, miR-1287, miR-1909, miR-1911, miR-759, miR-3150, miR-3174, miR-3180, miR-3191, miR-3197, miR-4292, miR-2115, miR-4312, miR-92, 93 and miR-99. In some embodiments, the at least one miR is selected from the group consisting of: miR-10b, miR-138, miR-154, miR-155, miR-181, miR-215, miR-614, and miR-668.

In some embodiments, the MSC is derived from bone marrow, adipose tissue, amniotic placenta, chorionic placenta, or umbilical cord. In some embodiments, the MSC is derived from chorionic placenta or umbilical cord. In some embodiments, the MSC is derived from chorionic placenta.

Co-culturing of cells is well known to those skilled in the art. In some embodiments, the co-culturing is performed in muscle cell media. In some embodiments, the co-culturing is performed in MSC media. In some embodiments, co-culture is performed in trans-well plates, such that there is no mixing of cells, but the cells exchange secreted factors. As used herein, "conditioned media" refers to old media that had been on growing cells for at least 1 day. Such media contains secreted factors from the growing cells, such as, but not limited to soluble factors, exosomes, microsomes, and other extracellular vesicles. In some embodiments, the conditioned media had been on growing cells for at least 24, 48, 72, 96 or 120 hours. Each possibility represents a separate embodiment of the invention.

The term "extracellular vesicles", as used herein, refers to all cell-derived vesicles secreted from MSCs including but not limited to exosomes and microvesicles. "Exosome", as used herein, refers to cell-derived vesicles of endocytic origin, with a size of 50-100 nm, and secreted from MSCs. As a non-limiting embodiment, for the generation of exosomes cells are maintained with Opti-MEM and human serum albumin or 5% FBS that was depleted from exosomes.

"Microvesicles", as used herein, refers to cell-derived vesicles originating from the plasma membrane, with a size of 100-1000 nm, and secreted from MSCs.

Exosomes, extracellular vesicles, or microvesicles can be obtained by growing MSCs in culture medium with serum depleted from exosomes or in serum-free media such as OptiMeM and subsequently isolating the exosomes by ultracentrifugation. Other methods associated with beads, columns, filters and antibodies are also employed. In some embodiments, the cells are grown in hypoxic conditions or incubated in medium with low pH so as to increase the yield of the exosomes. In other embodiments, the cells are exposed to radiation so as to increases exosome secretion and yield. In some embodiments, the exosomes are suspended in appropriate media for administration.

In some embodiments, the incubation with a ROCK inhibitor is for at least 8 hours, 12 hours, 18 hours, 24 hours, 36 hours, or 48 hours. Each possibility represents a separate embodiment of the invention. In some embodiments, the MSC is incubated with a ROCK inhibitor for about 24 hours.

In some embodiments, the incubation with 5-AZA is for at least 8 hours, 12 hours, 18 hours, 24 hours, 36 hours, or 48 hours. Each possibility represents a separate embodiment of the invention. In some embodiments, the MSC is incubated with 5-AZA for about 24 hours.

In some embodiments, the media is MSC media. In some embodiments, the media is muscle cell media. In some embodiments, the media is stem cell media. Such medias are well known in the art, and include but are not limited to, Skeletal Muscle Cell Media (Promocell), Vascular Smooth Muscle Cell Growth Kit, (ATCC), Smooth Muscle Cell Medium (Promocell), Smooth Muscle Cell Medium Supplement Kit (Cell Biologics), MesenPRO RS Medium (ThermoFisher), StemPro MSC SFM (ThermoFisher), and NutriStem MSC XF Medium (Biological Industries).

Introduction of a gene, RNA, nucleic acid or protein into a live cell will be well known to one skilled in the art. As used herein, "introduction" refers to exogenous addition of a gene, protein or compound into a cell. It does not refer to increasing endogenous expression of a gene, protein or compound. Examples of such introduction include, but are not limited to transfection, lentiviral infection, nucleofection, or transduction. In some embodiments, the introducing occurs ex vivo. In some embodiments, the introducing occurs in vivo. In some embodiments, the introducing occurs in vivo or ex vivo. In some embodiments, the introduction comprises introducing a vector comprising the gene of interest.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, introduction of a gene of interest comprises introduction of an inducible vector, wherein administration of a drug to the cell will induce expression of the gene of interest. Drug inducible vectors are well known in the art, some non-limiting examples include tamoxifen-inducible, tetracycline-inducible and doxycycline-inducible. In some embodiments, the inducible-vector is introduced to the MSC ex-vivo and the MSC is contacted with the inducing drug in-vivo. In this way expression of the induced gene, and as a result priming or differentiation of the MSC, only occurs in-vivo. In some embodiments, priming or differentiation of the MSC only occurs after the MSC has homed to a location in the body of a subject.

In some embodiments, introducing comprises introducing a modified mRNA. The term "modified mRNA" refers to a stable mRNA that maybe introduced into the cytoplasm of the cell and will there be translated to protein. Such a mRNA does not require transcription for protein expression and thus will more quickly produce protein and is subject to less regulation. Modified mRNAs are well known in the art.

In some embodiments, the cell of the invention is produced by combining protocols B and C. In some embodiments, the cell of the invention is produced by introducing into an MSC any one of NANOG, SOX2, KLF4, OCT4 or a combination thereof and incubating the MSC with 5-AZA. In some embodiments, the cell of the invention is produced by introducing Nanog into an MSC and incubating the MSC with 5-AZA.

The term "acidic medium" as used herein, refers to media in which the pH is at or below 6.0. In acidic medium, the growth media could have a pH of about 6.0, 5.5, 5.0, 4.5, 4.0, 3.5, or 3.0. Each possibility represents a separate embodiment of the invention. In some embodiments, the incubation with acidic media is for at least 15 minutes, 30 minutes, 45 minutes, 60 minutes, 90 minutes, or 120 minutes. Each possibility represents a separate embodiment of the invention. In some embodiments, the MSC is incubated in an acidic media for about 1 hour. In some embodiments, the acidic media has a pH of about 6. In some embodiments, the acid media has a pH between 5 and 6.

The term "hypoxia" or "hypoxic conditions" as used herein refers to a state in which the body, a region of the body, or cells are deprived of an adequate supply of oxygen. In some embodiments, the cells are grown in culture, in a hypoxia control chamber, wherein oxygen levels can be closely controlled. In hypoxia, oxygen levels may be below 5%, below 4.5%, below 4%, below 3.5%, below 3%, below 2.5%, below 2%, below 1.5%, below 1%, below 0.5%, or below 0.1%. Each possibility represents a separate embodiment of the invention. In some embodiments, hypoxia refers to an oxygen level between 2 and 4%. In some embodiments, the incubation with hypoxia is for at least 8 hours, 12 hours, 18 hours, 24 hours, 36 hours, or 48 hours. Each possibility represents a separate embodiment of the invention. In some embodiments, the MSC is incubated in hypoxic conditions for about 24 hours.

In some embodiments, a cell of the invention is produced by performing Protocol D followed by Protocol E. In some embodiments, a cell of the invention is produced by introducing Nanog into an MSC and then performing Protocol D, Protocol E, or both Protocols D and E. In some embodiments, a cell of the invention is produced by incubating an MSC with a) a ROCK inhibitor, b) acidic media or hypoxia, and c) any one of: a low adherence plate; media with low serum, supplemented with FGF or EGF; medium containing a small molecule selected from the group consisting of: a ROCK inhibitor, STAT3, an NF-KB activator, CHIR99021, metformin, tranylcypromine, a Gsk3 inhibitor, 3-deazaneplanocin A, an mTor inhibitor, a TGFβ inhibitor, Thiazovivin, A83-01, LiCl, SB431542, 5-AZA, rapamycin, ERK activators and valporic acid; and a combination thereof. In some embodiments, a cell of the invention is produced by a) introducing Nanog into an MSC incubating, b) incubating with a ROCK inhibitor, c) incubating in acidic media or hypoxia, and d) incubating with any one of: a low adherence plate; media with low serum, supplemented with FGF or EGF; medium containing a small molecule selected from the group consisting of: a ROCK inhibitor, a STAT3 activator, a NF-KB activator, CHIR99021, metformin, tranylcypromine, a Gsk3 inhibitor, 3-deazaneplanocin A, an mTor inhibitor, a TGFβ inhibitor, Thiazovivin, A83-01, LiCl, SB431542, 5-AZA, rapamycin, ERK activators and valporic acid; and a combination thereof.

In some embodiments, growth of cells on a low adherence plate, comprises 3D cell culture. The term "3D cell culture" as used herein refers to cell culture wherein cells are permitted to grow or interact with their surroundings in all three dimensions. In some embodiments, this can be achieved by growing the cells on low adherence plates, bioreactors, or small capsules. In some embodiments, the cells grown in 3D culture will take the shape of a spheroid as they grow. In other embodiments, the cells will take the shape of an organoid. The term "organoid" as used herein refers to a three-dimensional organ-bud grown in vitro, that shows realistic micro-anatomy similar to the organ which it is modeling.

The term "GSK-3 inhibitor" as used herein refers to any compound, therapeutic or drug that interferes with the kinase function of Glycogen synthase kinase 3 A or Glycogen synthase kinase B and suppresses their ability to phosphorylate a target. This suppression can be at least 60%, at least 65%, at least 70%, at least 75%, at least 80%, at least 85%, at least 90%, at least 95%, at least 99% suppression deacetylase active. Many well characterized GSK-3 inhibitors are known in the art, for example CHIR99021 or LiCl. In some embodiments, the GSK-3 inhibitor is administered at a concentration of 1-5, 1-10, 1-15, 1-20, 0.5-1, 0.5-5, 0.5-10. 0.5-15, 0.5-20, 0.1-1, 0.1-5, 0.1-10, 0.1-15, or 0.1-20 μM. Each possibility represents a separate embodiment of the invention. In some embodiments, CHIR99021 is administered at a concentration of 1-10 μM. In some embodiments, the GSK-3 inhibitor is administered at a concentration of 1-5, 1-10, 1-15, 1-20, 5-10, 5-15, 5-20, 10-15, or 10-20 mM. Each possibility represents a separate embodiment of the invention. In some embodiments, LiCl is administered at a concentration of 5-10 mM.

mTOR inhibitors are well known in the art, and include PP242. Inhibition by such an inhibitor can be at least 60%, and least 65%, at least 70%, at least 75%, at least 80%, at least 85%, at least 90%, at least 95%, at least 99% inhibition of the mTOR pathway. In some embodiments, an mTOR inhibitor is administered at a concentration of 1-20, 1-15, 1-10, 1-5, 0.5-1, 0.5-5, 0.5-10. 0.5-15, 0.5-20, 0.1-1, 0.1-5, 0.1-10, 0.1-15, or 0.1-20 μM. Each possibility represents a separate embodiment of the invention. In some embodiments, PP242 is administered at a concentration of 1-10 μM.

TGFβ inhibitors are well known in the art and include RepSox, SB431542 and A83-01 among many others. Inhibition by such an inhibitor can be at least 60%, and least 65%, at least 70%, at least 75%, at least 80%, at least 85%, at least 90%, at least 95%, at least 99% inhibition of the TGFβ pathway. In some embodiments, a TGFβ inhibitor is administered at a concentration of 1-20, 1-15, 1-10, 1-5, 0.5-1, 0.5-5, 0.5-10. 0.5-15, 0.5-20, 0.1-1, 0.1-5, 0.1-10, 0.1-15, or 0.1-20 μM. Each possibility represents a separate embodiment of the invention. In some embodiments, A83-01 is administered at a concentration of 0.5-1 μM. In some embodiments, SB431542 is administered at a concentration of about 10 μM.

ROCK inhibitors are well known in the art and include Thiazovivin among many others. Inhibition by such an inhibitor can be at least 60%, and least 65%, at least 70%, at least 75%, at least 80%, at least 85%, at least 90%, at least 95%, at least 99% inhibition of the ROCK pathway. In some embodiments, a ROCK inhibitor is administered at a concentration of 1-20, 1-15, 1-10, 1-5, 0.5-1, 0.5-5, 0.5-10. 0.5-15, 0.5-20, 0.1-1, 0.1-5, 0.1-10, 0.1-15, or 0.1-20 μM. Each possibility represents a separate embodiment of the invention. In some embodiments, Thiazovivin is administered at a concentration of 1-10 μM.

ERK activators are well known in the art and include resveratrol and fistein.

In some embodiments, valporic acid is administered at a concentration of 1-20, 1-15, 1-10, 1-5, 0.5-1, 0.5-2, 0.5-3, 0.5-4, 0.5-5, 0.5-10. 0.5-15, 0.5-20, 0.1-1, 0.1-5, 0.1-10, 0.1-15, or 0.1-20 mM. Each possibility represents a separate embodiment of the invention. In some embodiments, valporic acid is administered at a concentration of 0.5-2 mM.

In some embodiments, rapamycin is administered at a concentration of 1-20, 1-15, 1-10, 1-5, 0.5-1, 0.5-2, 0.5-3, 0.5-4, 0.5-5, 0.5-10. 0.5-15, 0.5-20, 0.1-1, 0.1-5, 0.1-10, 0.1-15, or 0.1-20 nM. Each possibility represents a separate embodiment of the invention. In some embodiments, rapamycin is administered at a concentration of 1-10 nM.

In some embodiments, metformin is administered at a concentration of 1-20, 1-15, 1-10, 1-5, 0.5-1, 0.5-5, 0.5-10. 0.5-15, 0.5-20, 0.1-1, 0.1-5, 0.1-10, 0.1-15, or 0.1-20 mg/ml. Each possibility represents a separate embodiment of the invention. In some embodiments, metformin is administered at a concentration of about 10 mg/ml.

In some embodiments, tranylcypromine is administered at a concentration of 1-20, 1-15, 1-10, 1-5, 0.5-1, 0.5-5, 0.5-10. 0.5-15, 0.5-20, 0.1-1, 0.1-5, 0.1-10, 0.1-15, or 0.1-20 μM. Each possibility represents a separate embodiment of the invention. In some embodiments, tranylcypromine is administered at a concentration of 1-10 μM.

In some embodiments, 3-deazaneplanocin A is administered at a concentration of 1-20, 1-15, 1-10, 1-5, 0.5-1, 0.5-5, 0.5-10. 0.5-15, 0.5-20, 0.1-1, 0.1-5, 0.1-10, 0.1-15, or 0.1-20 μM. Each possibility represents a separate embodiment of the invention. In some embodiments, 3-deazaneplanocin A is administered at a concentration of 1-10 μM.

In some embodiments, the incubations of Protocol E are for at least 30 minutes, 1 hour, 4 hours, 8 hours, 12 hours, 18 hours, 24 hours, 36 hours, or 48 hours. Each possibility represents a separate embodiment of the invention.

In some embodiments, the cell of the invention can be produced in combination with G-CSF treatment. The term "G-CSF treatment" as used herein refers to administration of G-CSF to cells or a subject, wherein the treatment mobilizes MSCs and CD34+ cells.

In some embodiments, the incubation with HGF or PDGFβ is for at least 30 minutes, 1 hour, 4 hours, 8 hours, 12 hours, 18 hours, 24 hours, 36 hours, or 48 hours. Each possibility represents a separate embodiment of the invention.

PCAT1 and NEAT1 are lncRNA and are known in the art. Introduction of a lncRNA can be performed by any method for introducing nucleic acid molecules into a cell. Such methods are described above.

In some embodiments, an inhibitor of a lncRNA is a siRNA. In some embodiments, an inhibitor of a lncRNA is a miR. In some embodiments, introducing an inhibitor comprises introducing a pre-miR or pre-siRNA.

In some embodiments, a cell of the invention is produced by performing Protocol 3 and further introducing into the MSC PCAT1 and NEAT1. In some embodiments, a cell of the invention is produced performing protocol 3 and further introducing into the MSC GAS5 and an inhibitor of PTENP1 expression. In some embodiments, a cell of the invention is produced by providing an MSC; contacting the MSC with at least one of an acidic medium, a ROCK inhibitor, or 5-AZA; introducing into the MSC at least one growth factor selected from: PDGFAA, PDGFBB, EGF, VEGF, TGFβ, and IGF1; and introducing into the MSC PCAT1 and NEAT1 or GAS5 and an inhibitor of PTENP1 expression.

In some embodiments, a cell of the invention is produced by incubating an MSC with acidic media, hypoxia, a ROCK inhibitor, or 5-AZA followed by performing Protocol 4.

In some embodiments, a cell of the invention is produced by performing Protocol 5 and further introducing into said MSC at least one lncRNA selected from the group consisting of MALAT1, MEG3, NEAT1, EGO, GAS5, KRASP1, LOC28519, BC200, and H19. In some embodiments, a cell of the invention is produced by performing Protocol 5 and further down regulating in said MSC expression of at least one of ANRIL, PTENP1 and aHIF. In some embodiments, the cell of the invention is produced by performing Protocol 5 or any process comprising Protocol 5, and further down-regulating the expression of at least one of ANRIL, PTENP1 and αHIF in said MSC. In some embodiments, the cell produced by Protocol 5, or by a procedure comprising Protocol 5, displays a satellite cell phenotype.

In some embodiments, down-regulation of expression is achieved by introducing into a cell an inhibitor of the expression. In some embodiments, an inhibitor of expression is selected from a miR, a pre-miR or siRNA. In some embodiments, down-regulation is achieved by genomic alteration such as by CRISPR or sleeping beauty technology.

In some embodiments, a cell of the invention is produced by performing at least one of Protocols A-E and then performing any one of Protocols 1-6. In some embodiments, a cell of the invention is produced by priming and MSC and then performing any one of Protocols 1-6. In some embodiments, a cell of the invention is produced by priming an MSC and then differentiating said MSC to a hybrid cell.

In some embodiments, a cell of the invention expresses at least one stemness markers selected from the group consisting of: SOX2, KLF4, OCT4 and NANOG. In some embodiments, a cell of the invention expresses a plurality of stemness markers selected from the group consisting of: SOX2, KLF4, OCT4 and NANOG. In some embodiments, a cell of the invention produced by any process comprising any one of Protocols A-E, expresses at least one stemness markers selected from the group consisting of: SOX2, KLF4, OCT4 and NANOG. In some embodiments, a cell of the invention produced by any process comprising any one of Protocols A-E, expresses a plurality of stemness markers selected from the group consisting of: SOX2, KLF4, OCT4 and NANOG.

In some embodiments, a cell of the invention secretes at least one trophic factor selected from: VEGF, GDNF and IGF1. In some embodiments, a cell of the invention produced by any process comprising any one of Protocols 1-6, expresses at least one trophic factor selected from: VEGF, GDNF and IGF1.

In some embodiments, a cell of the invention is produced by performing at least one of the protocols described herein and further determining or detecting the presence of an MSC phenotype and a muscle cell phenotype in the cell. In some embodiments, detecting comprises detecting the presence of an MSC protein marker. In some embodiments, detecting comprises detecting the presence of a muscle protein marker. In some embodiments, a cell of the invention is produced by performing at least one of the protocols described herein and further selecting a cell that is confirmed to have an MSC phenotype and a muscle cell phenotype.

By another aspect, the invention provides methods of producing the cells of the invention, the methods comprise performing at least one of the protocols described herein. In some embodiments, the invention provides a method of producing a cell of mixed character comprising an MSC phenotype and a muscle cell phenotype, the method comprising performing at least one of Protocols 1-6 and A-E.

Additions to the Cells

In some embodiments, the cells of the invention comprise a muscle cell targeting moiety on the cell's surface or a surface of the cell's extracellular vesicles. In some embodiments, the cells of the invention comprise a muscle cell targeting moiety. In some embodiments, the muscle cell targeting moiety comprises any one of: a ligand to caveolin3, M-cadherin, a ligand to the nicotinic acetylcholine receptor, a mutant dominant negative form of myostatin, and angiotensin II type 1. In some embodiments, the dominant negative from of myostatin propeptide comprises the C313Y mutation of myostatin. In some embodiments, the targeting moiety comprises a fusion protein comprising any one of the above described molecules fused to CD63 or CD81. In some embodiments, the muscle cell-targeting moiety comprises M-cadherin.

In some embodiments, the muscle cell targeting moiety is introduced into the cell by transfection. In some embodiments, the targeting moiety is introduced into the cell in a vector. In some embodiments, the targeting moiety is introduced to allow expression in the plasma membrane. In some embodiments, expression in the plasma membrane is expression of the outer surface of the plasma membrane. In some embodiments, the targeting moiety is introduced to allow expression in the membrane of exosomes and other extracellular vesicles.

In some embodiments, a cell of the invention comprises a therapeutic agent. In some embodiments, the therapeutic agent is a muscle therapeutic agent. In some embodiments, the therapeutic agent is selected from the group consisting of: a drug, a read-through drug, an RNA, a DNA molecule, a vector, an exon skipping oligonucleotide, a microRNA (miR), a small interfering RNA (siRNA) an antagomir, a long noncoding RNA (lncRNA) and a virus.

In some embodiments, the RNA is a modified MyoD mRNA. In some embodiments, the therapeutic is an inhibitor of a miR selected from: miR-424, miR-195, miR-16, miR-497, miR-135, miR-6793, miR-2, let-7, miR-133b and a combination thereof. In some embodiments, the antagomir is selected from the group consisting of: anti-miR-424, anti-miR-195, anti-miR-16, anti-miR-497, anti-miR-135, anti-miR-6793, anti-miR-21, anti-miR-133b and a combination thereof. In some embodiments, the antagomir is selected from anti-let 7 and anti-miR-133b. In some embodiments, the antagomir is anti-let 7.

In some embodiments, the drug is selected from oxytocin, melatonin, G-CSF, bortezomib and metformin. In some embodiments, the drug is a drug that increases expression of utrophin.

In some embodiments, the antagomir, hybridizes to a miR that targets dystrophin. In some embodiments, the antagomir hybridizes to a miR selected from the group consisting of: miR-606, miR-6893, miR-521, miR-3646 and miR-214. In some embodiments, the antagomir is anti-miR-214. In some embodiments, the cell comprises anti-miR-214, and microdystrophin or dystrophin.

In some embodiments, the virus is an adeno associated virus (AAV) carrying DNA encoding for at least one of: dystrophin, utrophin, lncRNA, CCAT1, Hur and IGFBP123. In some embodiments, the siRNA is directed against a mutant form of SOD1 associated with ALS. In some embodiments, the siRNA is directed against other mutant genes or proteins associated with ALS.

Pharmaceutical Compositions

By another aspect, the invention provides an isolated extracellular vesicle secreted by any of the cells of the invention. In some embodiments, the extracellular vesicle is an exosome. Methods of isolating extracellular vesicles are known to those of skill in the art and have been described herein.

By another aspect there is provided a pharmaceutical composition comprising any one of: a cell of mixed character of the invention, an extracellular vesicle of the invention, and a combination thereof. In some embodiments, the pharmaceutical composition further comprises a pharmaceutically acceptable carrier or adjuvant.

As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

Methods of Treatment Comprising Cells of Mixed Character

By another aspect, there is provided a method of treating, preventing or ameliorating a muscle-associated disease or muscle damage in a subject in need thereof, the method comprising administering a pharmaceutical composition of the invention to the subject, thereby treating, preventing or ameliorating the muscle-associated disease or muscle damage.

By another aspect, there is provided a pharmaceutical composition of the invention for use in treating, preventing or ameliorating a muscle-associated disease or muscle damage. By another aspect, there is provided use of the pharmaceutical compositions of the invention for the treatment, prevention or amelioration of a muscle-associated disease or muscle damage. By another aspect, there is provided a pharmaceutical composition of the invention for use in the treatment, prevention or amelioration of a muscle-associated disease or muscle damage.

In some embodiments, the composition comprises a cell derived from an MSC that is allogenic or autologous to the subject.

In some embodiments, treating or treatment comprises increasing muscle regeneration. In some embodiments, treating or treatment comprises decreasing fibrosis. In some embodiments, treating or treatment comprises increasing expression of utrophin in a muscle. In some embodiments, treating or treatment comprises increasing expression of dystrophin in a muscle. In some embodiments, ameliorating or amelioration comprises delaying the onset of symptoms in a subject.

By another aspect, there is provide a method of increasing expression of utrophin or dystrophin in muscle cells, comprising administering a pharmaceutical composition of the invention to the muscle cells, thereby increasing expression of utrophin or dystrophin in the muscle cells. By another aspect, there is provided a pharmaceutical composition of the invention for use in increasing expression of utrophin or dystrophin in muscle cells.

In some embodiments, the muscle cells are in culture. In some embodiments, the muscle cells are in a subject. In some embodiments, the muscle cells are in vitro or in vivo.

By another aspect, there is provided a method of increasing muscle generation in a subject in need thereof, the method comprising administering a pharmaceutical composition of the invention to the subject, thereby increasing muscle regeneration in a subject in need thereof. By another aspect, there is provided a pharmaceutical composition of the invention for use in increasing muscle generation. In some embodiments, the muscle generation is muscle regeneration. In some embodiments, the muscle is in culture. In some embodiments, the muscle is in a subject. In some embodiments, the muscle is in vitro or in vivo.

As used herein, the term "muscle-associated disease" refers to any disease or disorder than has a muscle component, or effects muscle function or health. Diseases that are associated with muscle symptoms are well known in the art, and include diseases of the muscle itself, diseases or the skeleton, diseases of neurons that enervate the muscle, mitochondrial diseases, and energy homeostatic diseases to name a few. In some embodiments, the muscle-associated disease or damage is selected from the group consisting of: a motor neuron disease, a peripheral neuron disease, a muscular dystrophy, spinal cord injury, muscle wasting, cardiac muscle injury, cardiac fibrosis, inflammatory myopathy, myasthenia gravis, sarcopenia, cachexia, and skeletal muscle injury. In some embodiments, the muscle-associated disease is selected from the group consisting of: amyotrophic lateral sclerosis (ALS), cachexia, cardiac fibrosis, and a muscular dystrophy. In some embodiments, the muscular dystrophy is Duchene's muscular dystrophy (DMD).

In some embodiments, the muscle-associated disease is ALS and the method further comprises administering at least one MSC differentiated toward an astrocyte phenotype or a neuronal stem cell (NSC) phenotype. MSCs can be differentiated by many methods known to one of skill in the art. In some embodiments, differentiation to an astrocyte phenotype is performed as described in US Application US20150037298. In some embodiments, differentiation to a NSC phenotype is performed as described in US Application US20150037299.

In some embodiments, the muscle-associated disease is DMD, and the method further comprises administering any one of: an undifferentiated MSC, the extracellular vesicles of an undifferentiated MSC, and a combination thereof.

In some embodiments, the cells of the invention or their extracellular vesicles are targeted to skeletal muscle, heart, or diaphragm by exposing the appropriate body area of the subject to shockwave, focused ultrasound or low laser therapy.

By another aspect, there is provided a method of increasing engraftment of cells into a subject in need thereof, the method comprising co-administering with said cells any one of: a pharmaceutical composition of the invention, a pharmaceutical composition comprising unmodified MSCs, and a combination thereof, thereby increasing engraftment of the cells. By another aspect, there is provided a composition comprising any one of: a cell of mixed character of the invention, an unmodified MSC, and a combination thereof, for use in increasing engraftment of cells.

In some embodiments, the cell is allogenic or autologous to the subject. In some embodiments, the unmodified MSC is derived from umbilical cord or chorionic placenta. In some embodiments, the unmodified MSC is derived from chorionic placenta.

In some embodiments, the cell to be grafted is selected from the group consisting of: a myoblast, a satellite cell, a mesangioblast, a cardiac stem cell, an astrocyte and a neuronal stem cell. In some embodiments, the cell to be grafted is selected from the group consisting of: a myoblast, a satellite cell, an astrocyte and a neuronal stem cell. In some embodiments, the ratio of administered MSCs or cells of a mixed character to engraftment cells is between 1:1 to 2:1.

By another aspect, there is provide a method of increasing expression of utrophin or dystrophin in muscle cells, comprising administering to muscle cells a pharmaceutical composition comprising any one of: a pharmaceutical composition of the invention, an unmodified MSC, an exosome derived from an unmodified MSC, and a combination thereof, thereby increasing expression of utrophin or dystrophin in the muscle cells. By another aspect, there is provided a composition comprising any one of: a pharmaceutical composition of the invention, an unmodified MSC, an exosome derived from an unmodified MSC, and a combination thereof, for use in increasing expression of utrophin or dystrophin in muscle cells.

In some embodiments, the muscle cells are in culture. In some embodiments, the muscle cells are in a subject. In some embodiments, the muscle cells are in vitro or in vivo. In some embodiments, the unmodified MSC is derived from umbilical cord or chorionic placenta. In some embodiments, the unmodified MSC is derived from chorionic placenta.

Kits of the Invention

By another aspect, there is provided a kit comprising: MSC media and at least one differentiation agent. By another aspect, there is provided a kit comprising: an umbilical cord MSC or a chorionic MSC and at least one differentiation agent. In some embodiments, the kit further comprises MSC media.

By another aspect, there is provided a kit comprising any one of: a cell of mixed character of the invention, an isolated extracellular vesicle of the invention, a combination thereof.

As used herein, the term "differentiation agent" refers to any of the substances described herein for use in protocols A-E and 1-6. In some embodiments, the kit comprises at least 1, 2, 3, 4, 5 or 6 differentiation agents. Each possibility represents a separate embodiment of the invention.

In some embodiments, the differentiation agent is selected from the group consisting of: a stemness factor, a ROCK inhibitor, a STAT3 activator, an NF-KB activator, CHIR99021, metformin, tranylcypromine, a Gsk3 inhibitor, 3-deazaneplanocin A, an mTor inhibitor, a TGFβ inhibitor, Thiazovivin, A83-01, LiCl, SB431542, 5-AZA, rapamycin, ERK activators, valporic acid. In some embodiments, the stemness factor is selected from the group consisting of: NANOG, SOX2, KLF4, OCT4 and a combination thereof. In some embodiments, the differentiation agent is selected from the group consisting of: a growth factor, a lncRNA, a transcription factor and a miR. In some embodiments, the growth factor is selected from the group consisting of: HGF, PDGFβ, PDGFAA, PDGFBB, EGF, VEGF, TGFβ, IGF1 and a combination thereof. In some embodiments, the transcription factor is selected from the group consisting of: MYF5, PAX3, PAX7, MyoD and PAX3, MyoD and PAX7, and MyoD and MYF5. In some embodiments, the differentiation agent is selected from: a muscle cell, a muscle cell exosome, dystrophin, microdystrophin, and utrophin. In some embodiments, the lncRNA is selected from the group consisting of: PCAT1, NEAT1, GAS5, BIL, PAR5, BIC, DISC2, GAS5DLG2AS, 7SK, Y1, LINCRNA, SFMBT2, Y4, SCAB, MALAT1, MEG3, EGO, KRASP1, LOC28519, BC200, and H19. In some embodiments, the lncRNA is selected from PAR5, DISC2 and PCAT1. In some embodiments, the miR is selected from the group consisting of: miR-10b, miR-22, miR-122, miR-125a, miR-140-5p, miR-143, miR-145, miR-146a, miR-148b, miR-150, miR-155, miR-181b, miR-215, miR-296, miR-330, miR-370, miR-429, miR-520, miR-524, miR-543, miR-550, miR-561, miR-564, miR-582, miR-583, miR-587, miR-613, miR-614, miR-629, miR-634, miR-645, miR-646, miR-649, miR-661, miR-662, miR-663, miR-665, miR-668, miR-671, miR-887, miR-1183, miR-1224, miR-1225, miR-1228, miR-1234, miR-1246, miR-1247, miR-1257, miR-1258, miR-1268, miR-1269, miR-1289, miR-1287, miR-1909, miR-1911, miR-759, miR-3150, miR-3174, miR-3180, miR-3191, miR-3197, miR-4292, miR-2115, miR-4312, miR-92, 93 and miR-99. In some embodiments, the miR is selected from the group consisting of: miR-10b, miR-138, miR-154, miR-155, miR-181, miR-215, miR-614, and miR-668.

In some embodiments, the kit further comprises a muscle cell-targeting moiety. In some embodiments, the muscle cell targeting moiety comprises any one of: a ligand to caveolin3, M-cadherin, a ligand to the nicotinic acetylcholine receptor, a mutant dominant negative form of myostatin, and angiotensin II type 1. In some embodiments, the dominant negative from of myostatin propeptide comprises the C313Y mutation of myostatin. In some embodiments, the targeting moiety comprises a fusion protein comprising any one of the above described molecules fused to CD63 or CD81. In some embodiments, the muscle cell-targeting moiety comprises M-cadherin.

In some embodiments, the kit further comprises a therapeutic agent. In some embodiments, the therapeutic agent is a muscle therapeutic agent. In some embodiments, the therapeutic agent is selected from the group consisting of: a drug, a read-through drug, an RNA, a DNA molecule, a vector, an exon skipping oligonucleotide, a microRNA (miR), a small interfering RNA (siRNA) an antagomir, a long noncoding RNA (lncRNA) and a virus.

In some embodiments, the RNA is a modified MyoD mRNA. In some embodiments, the therapeutic is an inhibitor of a miR selected from: miR-424, miR-195, miR-16, miR-497, miR-135, miR-6793, miR-2, let-7, miR-133b and a combination thereof. In some embodiments, the antagomir is selected from the group consisting of: anti-miR-424, anti-miR-195, anti-miR-16, anti-miR-497, anti-miR-135, anti-miR-6793, anti-miR-21, anti-miR-133b and a combination thereof. In some embodiments, the antagomir is selected from anti-let 7 and anti-miR-133b. In some embodiments, the antagomir is anti-let 7.

In some embodiments, the drug is selected from oxytocin, melatonin, G-CSF, bortezomib and metformin. In some embodiments, the drug is a drug that increases expression of utrophin.

In some embodiments, the antagomir, hybridizes to a miR that targets dystrophin. In some embodiments, the antagomir hybridizes to a miR selected from the group consisting of: miR-606, miR-6893, miR-521, miR-3646 and miR-214. In some embodiments, the antagomir is anti-miR-214. In some embodiments, the cell comprises anti-miR-214, and micro-dystrophin or dystrophin.

In some embodiments, the virus is an adeno associated virus (AAV) carrying DNA encoding for at least one of: dystrophin, utrophin, lncRNA, CCAT1, Hur and IGFBP123. In some embodiments, the siRNA is directed against a mutant form of SOD1 associated with ALS. In some embodiments, the siRNA is directed against other mutant genes or proteins associated with ALS.

Methods of Treatment Comprising Unmodified MSCs

By another aspect, there is provided a method of treating, preventing or ameliorating a muscular dystrophy, fibrosis, or cachexia, the method comprising administering an undifferentiated MSC, an extracellular vesicle of an undifferentiated MSC or a combination thereof. By another aspect, there is provided a composition comprising any one of, an undifferentiated MSC, an extracellular vesicle of an undifferentiated MSC or a combination thereof, for use in treating, preventing or ameliorating a muscular dystrophy, fibrosis, or cachexia. By another aspect, there is provided a composition comprising any one of, an undifferentiated MSC, an extracellular vesicle of an undifferentiated MSC or a combination thereof, for use in the treatment, prevention or amelioration of a muscular dystrophy, fibrosis, or cachexia.

In some embodiments, the MSC is derived from umbilical cord or chorionic placenta. In some embodiments, the MSC is derived from chorionic placenta. In some embodiments, the muscular dystrophy is DMD. In some embodiments, fibrosis is cardiac fibrosis.

Chorionic MSCs are well known in the art. In some embodiments, chorionic MSCs or their secreted vesicles can be identified by examining the expression of any of the following: a) one or more long non-coding RNAs (lncRNAs) selected from the group consisting of: SCAB, TU00176, LINC-VLDLR and optionally ROR; b) one or more miRNA selected form the group consisting of mir-3163, mir-128, mir-27a, mir-27b, mir-148a, mir-148b, mir-152, mir-651, mir-9, mir-466, mir-577, mir-380, mir-2909, mir-4803, mir-556-3p, mir-182, mir-4677-5p, mir-4672, mir-3942-5p, mir-4703-5p, mir-4765, mir-4291, mir-144, mir-1206, mir-4435, mir-452, mir-4676-3p, mir-25, mir-32, mir-363, mir-367, mir-92a, mir-92b, mir-340, mir-3620, mir-4324, mir-4789-5p, mir-346, mir-944, mir-3180-5p, mir-202, mir-511, mir-4326, mir-578, mir-4312, mir-4282, mir-597, mir-3689d, mir-2116, mir-4517, mir-199a-3p, mir-199b-3p, mir-3129-5p, mir-520d-5p, mir-524-5p, mir-203, mir-3942-3p, mir-501-5p, mir-143, mir-4770, mir-4422, mir-4495, mir-1271, mir-96, mir-1297, mir-26a, mir-26b, mir-4465, mir-4273, mir-1294, let-7a, let-7b, let-7c, let-7d, let-7e, let-7f, let-7g, let-7i, mir-4458, mir-4500, mir-98, mir-4652-3p, mir-4716-5p, mir-513a-5p, mir-223, mir-4288, mir-455-5p, mir-632, mir-4477b, mir-142-3p, mir-561, mir- 4698, mir-3140-3p, mir-3662, mir-410, mir-376a, mir-376b, mir-1270, mir-620, mir-515-5p, mir-875-5p, mir-140-5p, mir-4256, mir-30a, mir-30b, mir-30c, mir-30d, mir-30e, mir-4254, mir-515-3p, mir-519e, mir-2964a-5p, mir-2115, mir-520a-5p, mir-525-5p, mir-1244, mir-3190, mir-548a-5p, mir-548ab, mir-548ak, mir-548b-5p, mir-548c-5p, mir-548d-5p, mir-548h, mir-548i, mir-548j, mir-548w, mir-548y, mir-559, mir-2681, mir-3671, mir-375, mir-4789-3p, mir-3143, mir-125a-5p, mir-125b, mir-4319, mir-5096, mir-338-5p, mir-493, mir-3153, mir-875-3p, mir-516a-3p, mir-323-3p, mir-3065-5p, mir-4762-3p, mir-3617, mir-641, mir-124, mir-506, mir-4531, mir-4512, mir-570, mir-4679, mir-3144-3p, mir-4777-3p, mir-4732-3p, mir-3177-5p, mir-548n, mir-4328, mir-2355-3p, mir-4330, mir-4524, mir-4719, mir-3976, mir-544, mir-3607-3p, mir-581, mir-205, mir-4731-3p, mir-4801, mir-3667-5p, mir-1245b-3p, mir-4760-3p, mir-137, mir-3194-3p, mir-342-3p, mir-2682, mir-449c, mir-532-3p, mir-4305, mir-1, mir-206, mir-613, mir-676, mir-1296, mir-196a, mir-196b, mir-3941, mir-4795-3p, mir-431, mir-607, mir-548k, mir-4464, mir-4748, mir-654-3p, mir-544b, mir-3074-5p, mir-3115, mir-4635, mir-4323, mir-548t, mir-4680-5p, mir-133a, mir-133b, mir-600, mir-1208, mir-4708-5p, mir-3123, mir-4251, mir-4307, mir-3185, mir-582-5p, mir-4436b-3p, mir-378, has, mir-378b, mir-378c, mir-378d, mir-378e, mir-378f, mir-378h, mir-378i, mir-422a, mir-4460, mir-200b, mir-200c, mir-429, mir-4470, mir, 1245b-5p, mir-3142, mir-576-3p, mir-548m, mir-4666-3p, mir-325, mir-330-3p, mir-3690, mir-548a-3p, mir-548e, mir-548f, mir-4709-5p, mir-532-5p, mir-539, mir-4303, mir-4302, mir-300, mir-381, mir-4645-3p, mir-3910, mir-1301, mir-5047, mir-188-5p, mir-3974, mir-3923, mir-3686, mir-670, mir-2052, mir-548a1, mir-3200-3p, mir-4686, has, mir-3545-5p, mir-194, mir-498, mir-3913-3p, mir-3168, mir-499-3p, mir-499a-3p, mir-656, mir-4762-5p, mir-4496, mir-141, mir-200a, mir-3529, mir-379, mir-3691-3p, mir-520f, mir-503, mir-4477a, mir-513a-3p, mir-3149, mir-3927, mir-1283, mir-4767, mir-487b, mir-4637, mir-19a, mir-19b, mir-4683, mir-548an, mir-1200, mir-4638-3p, mir-1825, mir-522, miR-24, miR-22-3p, miR-92, miR-378, miR-93; c) one of more secreted factors selected from the group consisting of HGF, wnt2, GDNF, Osteoprotegerin, MIP3α, NT-3, IL-6, IL-8, FGF7, NT-4, EGFL6 and optionally LIF and BDNF; d) one of more surface markers selected from: TCR alpha-beta, CD55, LIFR, and ST6GALNAC5; e) one or more stemness and mesenchymal markers selected from: low YKL40 and KLF4; f) MSC-derived vesicle expression of one or more proteins selected from the group consisting of: COL4A2, LGALS3, SCUBE1, LGAS3, and S100A10; g) MSC-derived vesicle expression of one or more lncRNAs selected from the group consisting of BCMS, BIC, and optionally HAR1B; and h) a combination thereof.

In some embodiments, the chorionic MSCs may also be identified by cell-derived vesicles comprising one or more proteins selected from the group consisting of: CASK, COL3A1, B2M, CDH2, CTNNA1, DLG1, EGFR, F3, FARP1, GPC1, CDH2, CTNNA1, HAPLN1, LAMB1, LAMB2, LAMPC1, LGALS3BP, LOXL2, MCAM, NID1, OLXNB2, S100A6, TNC, WNT5A, and PLXNB2.

By another aspect, there is provided, a method of treating, preventing or ameliorating ALS in a subject in need thereof, the method comprising administering a pharmaceutical composition comprising any one of: an MSC differentiated toward an astrocyte phenotype, an MSC differentiated toward a neuronal stem cell phenotype and a combination thereof. By another aspect, there is provided a composition comprising any one of, an MSC differentiated toward an astrocyte phenotype, an MSC differentiated toward a neuronal stem cell phenotype and a combination thereof, for use in treating, preventing or ameliorating ALS. By another aspect, there is provided a composition comprising any one of, an MSC differentiated toward an astrocyte phenotype, an MSC differentiated toward a neuronal stem cell phenotype and a combination thereof, for use in the treatment, prevention, or amelioration of ALS.

In some embodiments, the MSC is derived from umbilical cord or chorionic placenta. In some embodiments, the MSC is derived from chorionic placenta.

In some embodiments, treating or treatment comprises increasing muscle regeneration. In some embodiments, treating or treatment comprises decreasing fibrosis. In some embodiments, treating or treatment comprises increasing expression of utrophin in a muscle. In some embodiments, treating or treatment comprises increasing expression of dystrophin in a muscle. In some embodiments, ameliorating or amelioration comprises delaying the onset of symptoms in a subject.

In some embodiments, the methods comprising untreated MSCs are performed with MSCs comprising a muscle cell-targeting moiety as described herein above. In some embodiments, the methods comprising untreated MSCs are performed with MSCs comprising a therapeutic agent as described herein above.

By another aspect, there is provided a method of diagnosing cachexia in a subject in need thereof, the method comprising: providing exosomes from the subject's serum, incubating the exosomes with a human immortalized cell line, and measuring one of cell death, and myosin heavy chain expression, wherein an increase in cell death or a decrease in myosin heavy chain expression indicates the subject has cachexia.

By another aspect, there is provided a method of detecting cachexic exosomes in a subject, the method comprising providing exosomes from the subject's serum, incubating the exosomes with a human immortalized cell line, and measuring one of cell death, and myosin heavy chain expression, wherein an increase in cell death or a decrease in myosin heavy chain expression indicates the presence of cachexic exosomes in the subject.

The definitions of certain terms as used in this specification are provided herein. Unless defined otherwise, all technical and scientific terms used herein generally have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

As used in this specification and the appended claims, the singular forms "a", "an" and "the" include plural referents unless the content clearly dictates otherwise. For example, reference to "a nucleic acid" includes a combination of two or more nucleic acids, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods
Preparation of Placenta-Derived MSCs

Placenta and umbilical cord MSCs were isolated from humans, canines and horses by the following protocol: The tissues were washed with PBS. The amniotic and the chorionic membrane were mechanically fragmented into small pieces and then submitted to enzymatic digestion in two stages. (1) Incubation with 0.25% trypsin/EDTA at 37° C. for 30 min in order to remove the epithelial cells. (2) Treatment with 0.1% collagenase IV for 60 min at 37° C. followed by inactivation with fetal calf serum. The cell suspension was then filtered through 100 μM filter and the centrifuged cells were seeded in 75 cm$^2$ Corning flasks in DMED medium/nutrient mixture F-12 (DMEM/F12) consisting of 15% fetal calf serum, 2 mM L-glutamine, 100 U/ml penicillin and 100 μg/ml streptomycin. Alternatively, cells were maintained in serum-free MSC medium. Similar procedures were employed for the preparation of MSCs from umbilical cord. After 2 weeks, the cells were incubated with Rock inhibitor for 1 day followed by incubation in hypoxic conditions for additional 24 hr. The cells were maintained in medium deprived of exosomes.

Exosome Isolation

Exosome isolation from cell culture media was performed at 4° C. by multi-step centrifugation. Briefly, media was centrifuged at 10,000×g for 30 minutes to remove large debris and then filtered through a 0.22 μm filter to remove small cell debris. The supernatant was then centrifuged at 100,000×g for 1-2 hours. Exosomes were identified by the expression of CD63, CD9 and ALIX by electron microscopy and by nanoparticle tracking analysis (NTA). Quantification of exosomes was analyzed by measuring the total protein concentration and by CD63 ELISA (SBI).

qRT PCR

Total RNA was extracted using an RNeasy midi kit according to the manufacturer's instructions (Qiagen). Reverse transcription reaction was carried out using 2 μg total RNA. A primer optimization step was tested for each set of primers to determine the optimal primer concentrations. Primers, 25 μL of 2×SYBR Green Master Mix (Invitrogen), and 30 to 100 ng cDNA samples were resuspended in a total volume of 50 μL PCR amplification solution. The primers used are listed in Table 1. Reactions were run on an ABI Prism 7000 Sequence Detection System (Applied Biosystems, Foster City, Calif.). Cycle threshold (Ct) values were obtained from the ABI 7000 software. S12 or ß-actin levels were also determined for each RNA sample as controls.

TABLE 1

| Gene | Forward | (SEQ ID NO:) | Reverse | (SEQ ID NO:) |
|---|---|---|---|---|
| OCT4 | atcagccacatcgcccagca | (1) | cccagcagcctcaaaatcct | (2) |
| SOX2 | tgggttcggtggtcaagtc | (3) | cgctctggtagtgctggga | (4) |
| S12 | tgctggaggtgtaatggacg | (5) | caagcacacaaagatgggct | (6) |
| TNFα | ggtgcttgttcctcagcctc | (7) | caggcagaagagcgtggtg | (8) |
| hDystrophin | tctcattgtttttaagccta | (9) | catctacgatgtcagtacttcca | (10) |
| CD105 | gcgcttgaacatcatcagcc | (11) | ggaacgcgtgtgcgagt | (12) |
| mDystrophin | tctcatcgtacctaagcctc | (13) | cagtgccttgttgacattgttcag | (14) |
| Irisin | tgaaagagatggggaggaacca | (15) | ggcagaagagggcaatgacac | (16) |
| RTVP1 | ccagttttcacataatacacggc | (17) | aagagcgtcaaagccagaaa | (18) |
| CD146 | aaacatccaggtcaaccccc | (19) | accactcgactccacagtct | (20) |
| CD271 | acctcatccctgtctattgc | (21) | ctgttggctccttgcttgtt | (22) |
| CD44 | ctccacctgaagaagattgt | (23) | aagatgtaacctcctgaagt | (24) |
| ITG7A | attccccagcaactcttctt | (25) | tacagcaaccacttcccatt | (26) |
| PAX7 | gaacctgacctcccactgaa | (27) | tcctgcctgcttacgccaac | (28) |
| MYOG | caaccaggaggagcgtgac | (29) | cagccgtgagcagatgat | (30) |
| DMD | atgatacgggacgaacaggg | (31) | tgaacttgccacttgcttga | (32) |
| MYF5 | cccacctccaactgctctga | (33) | caactggagagagagaagcc | (34) |
| MYH1 | caccccacatcttctccatc | (35) | ccttcttcttctccccagta | (36) |
| MyoD | ccgcagccgccttctatg | (37) | acaccgccgcactcttcc | (38) |
| MYF6 | tgataacggctaaggaagga | (39) | cacgatggaagaaaggca | (40) |

Surface Marker Analysis

Surface marker expression was measured by FACS analysis. Cells were dissociated using 0.25% Trypsin-EDTA (Life Technologies) or collected from the plates and were resuspended in phosphate buffered saline without calcium and magnesium to obtain single cell suspension. $3 \times 10^5$ cells were used for staining with the MSC isotype cocktail (Miltenyi Biotec) and a Human MSC Functional ID Kit (R&D Systems), which include both positive (CD73-APC, CD90-FITC, CD105-PE) and negative (CD34/CD45/CD14/CD20-PerCp) antibodies. The cells were incubated with the antibodies for 30 min at 4° C., washed 3 times with PBS and resuspended in 0.5 ml PBS. Cells were the analyzed in FACS Aria III instrument (BD BioSciences).

New Muscle Fiber Counts

Mice were injected with 25 μl of cardiotoxin in PBS into their TA muscle and sacrificed after 7 days. The muscle was dissected and stained for embryonic myosin heavy chain (MYH1), and cells positive for MYH1 with centrally located nuclei were scored as newly generated muscle. Alternatively, cells double positive for MyoD and Pax7 are considered asymmetrically dividing satellite cells and cells positive for NCAM are considered regenerating cells.

Exosome Loading

MSCs were transduced with the molecule to be loaded (miR, siRNA, pre-miR, shRNA, modified mRNA) by either lentiviral infection, or transfection using silMporter (Millipore). Exosomes are then isolated (see above) and examined to confirm expression of the molecule to be loaded.

Co-Transplantation

Human cells for engraftment were either transduced with a lentiviral vector expressing mCherry or GFP or loaded with Qdot 655 nanocrystals using the Qtracker 655 cell labeling kit (Thermo). Labeled cells were then mixed with MSCs in ratios from 1:1 to 2:1 (more labeled cells). $1 \times 10^5$ MSC were always used.

Muscle Cell Targeting Moiety

CH-MSCs were transfected with a M-cadherin and exosomes from those cells were collected (see above), labeled with a fluorescent dye and analyzed to confirm fluorescence. The exosomes were then administered to human muscle cells and human astrocytes in culture. After 28 hours, the cells were washed to remove unabsorbed exosomes, and the number of fluorescent cells (having taken up the exosomes) was measured.

Example 1: MSCs Increase Regeneration and Decrease Fibrosis

Use of mesenchymal stem cells (MSCs) from various tissues as a possible treatment for muscular dystrophies has been suggested (Markert C D, et al., 2009, PM&R, 1(6): 547-559; Rajput B S. et al., 2015, Journal of Stem Cells, 10(2): 141-156; Li P, et al., 2015, International Journal of Molecular Medicine, 35(4): 1051-1057) even as the underlying mechanism by which MSCs effect muscle health has been poorly understood. Mdx mice are widely used as an animal model for Duchenne's Muscular Dystrophy (DMD). In order to identify the MSC source with the optimal therapeutic effect on muscle functions in mdx mice, MSCs derived from bone marrow (BM), adipose tissue (AD), umbilical cord (UC) and the amnion (AM) and chorion (CH) of the placenta, or CD34+ hematopoietic progenitor cells, were injected ($5 \times 10^5$ cells per injection) into the quadriceps of mdx mice and expression of several key factors related to regeneration and fibrosis were examined after 4 weeks.

Figure 1B:
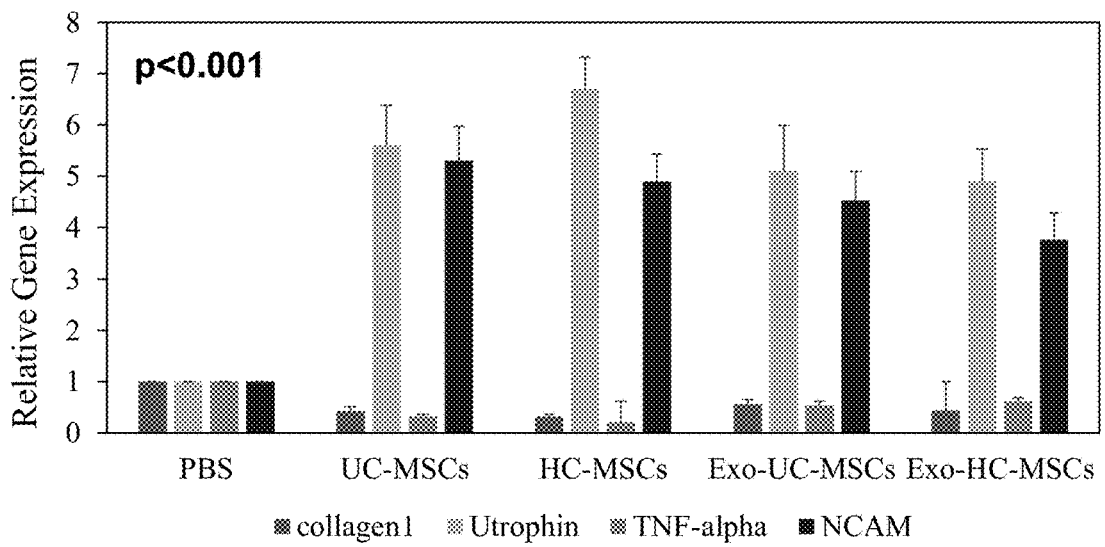
Figure 1C:
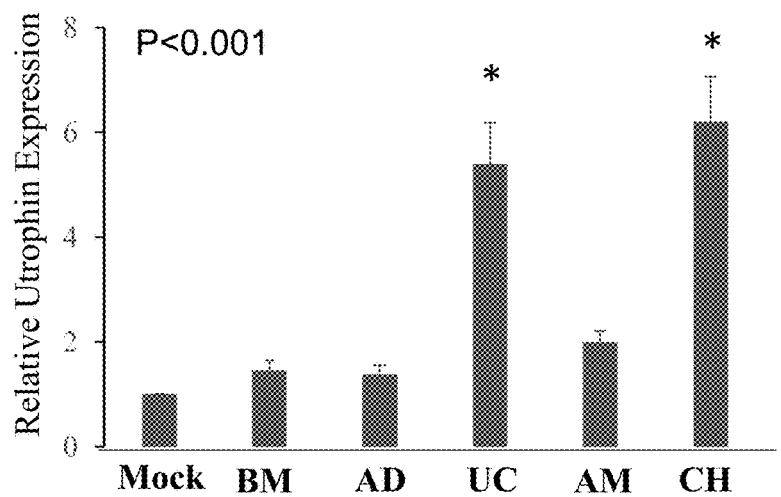
Figure 1D:
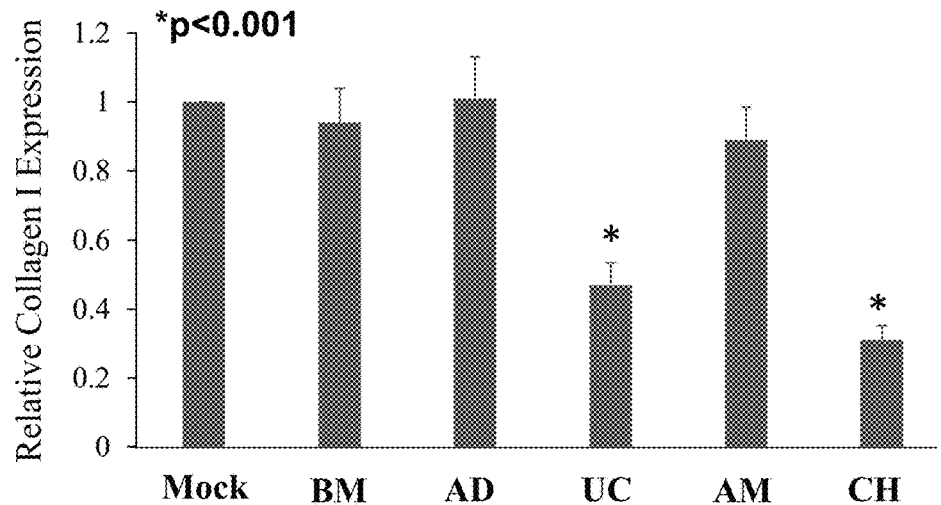

All tested cell types induced a significant increase in the mRNA expression in the quadricep of two markers of cellular regeneration: embryonic myosin heavy chain (MYH1, ~4-fold increase, data not shown), and NCAM (FIGS. 1A and 1B). In addition, UC- and CH-MSCs significantly increased the expression of Utrophin (FIGS. 1A-1C), a protein that can functionally replace dystrophin and therefore exerts a therapeutic effect in mdx mice and theoretically DMD patients. BM-, AD- and AM-MSCs caused only a very small not statistically significant increase in utrophin expression. Levels of VEGF and HIF1α were also increased (FIG. 1A). Additionally, UC- and CH-MSCs significantly reduced the expression of Collagen I, a marker of fibrosis, in the diaphragm and the heart, while BM-, AD- and AM-MSCs had no effect (FIGS. 1A-1B and 1D). Lastly, both UC-MSCs and HC-MSCs decreased the expression of inflammatory markers such as TNFα and INFγ (FIG. 1B), while lower effects were observed with BM and AD-derived MSCs.

Figure 1E:
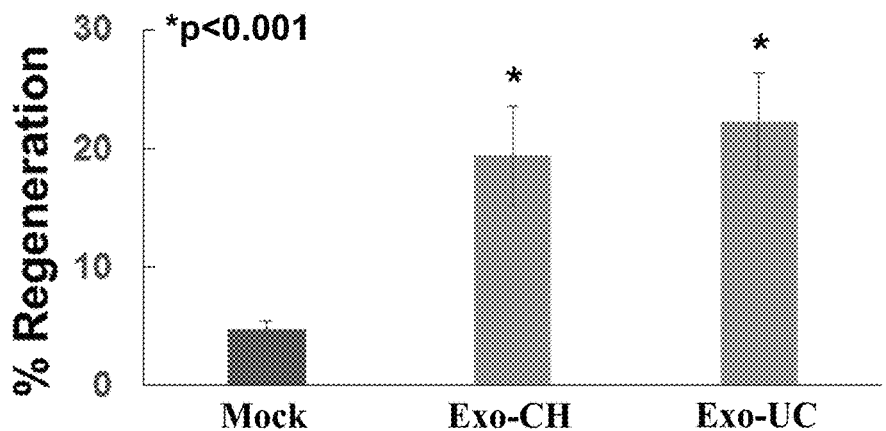

As muscle cells are part of the mesenchymal lineage, it is possible that the therapeutic value of MSC may come from their physically becoming part of the muscle syncytium and acting as a cellular replacement. However, MSCs also have a large secretome which might media its effects on muscles. To test if the gene expression changes observed in the mdx mouse were primarily due to MSC fusion or rather due to secreted factors, exosomes were purified from $5 \times 10^5$ UC- or CH-MSCs and injected into the quadriceps of the MDX mice. The same, although slightly reduced, gene expression changes were observed for all four genes tested when only exosomes were injected (FIG. 1B), further the amount of regeneration in the quadricep was significantly increased (FIG. 1E). This indicates that cell replacement is not the major source of therapeutic benefit conferred by the MSCs.

Figure 1F:
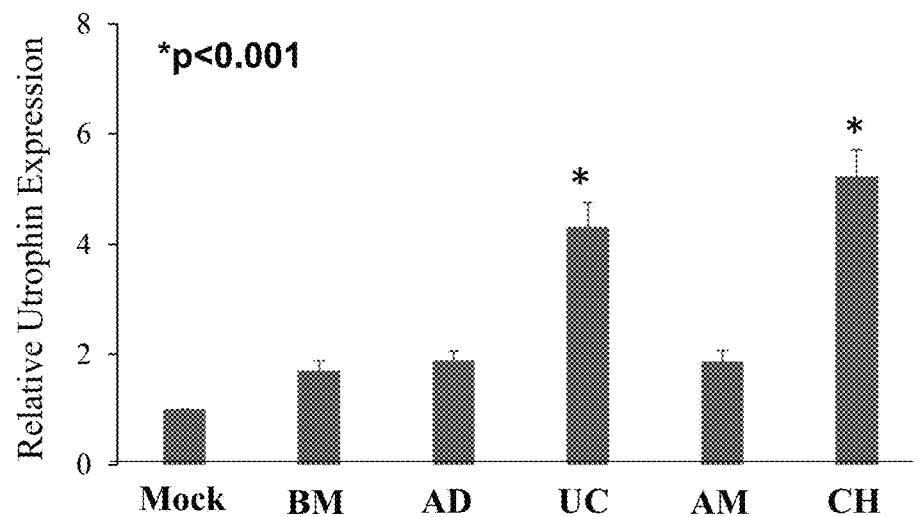
Figure 1G:
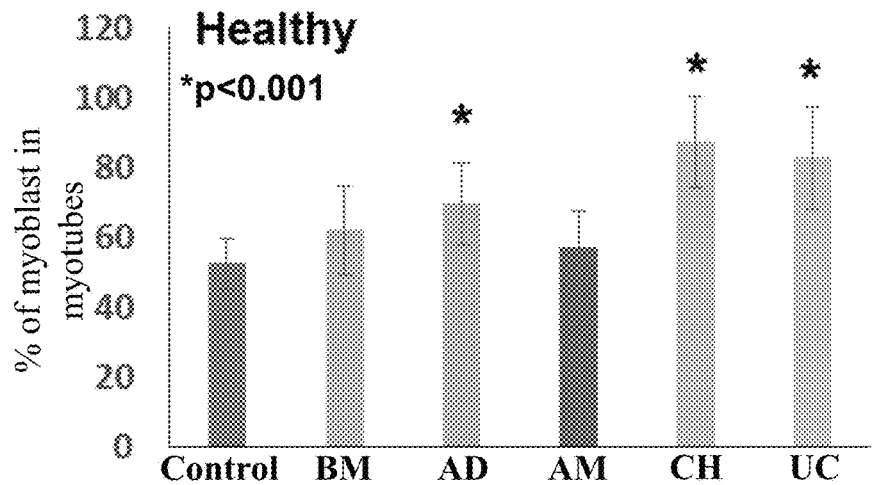
Figure 1H:
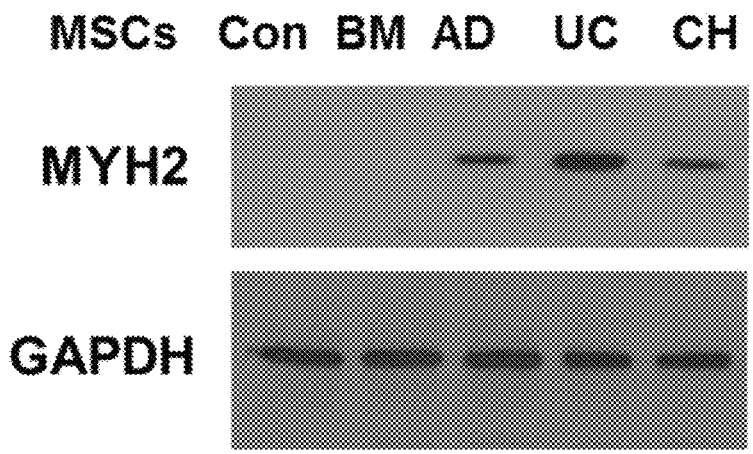
Figure 1I:
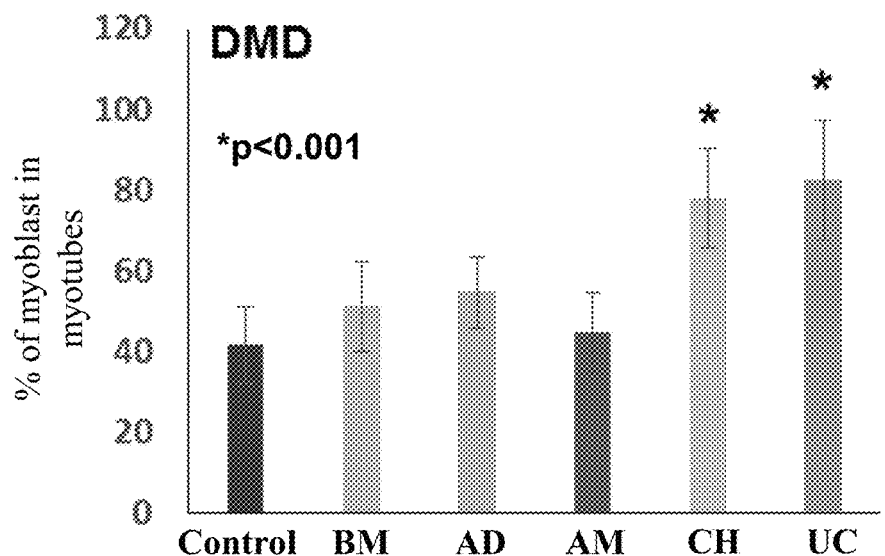
Figure 1J:
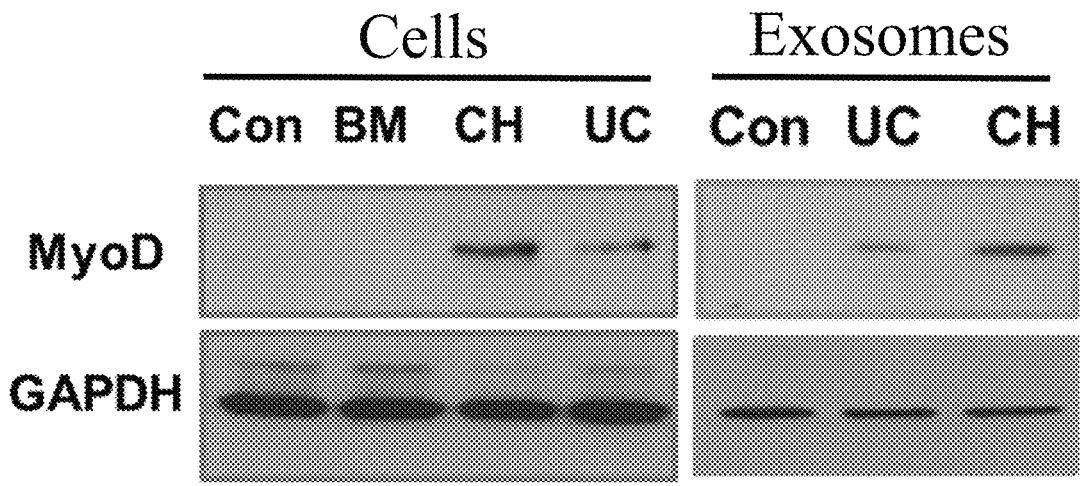
Figure 1K:
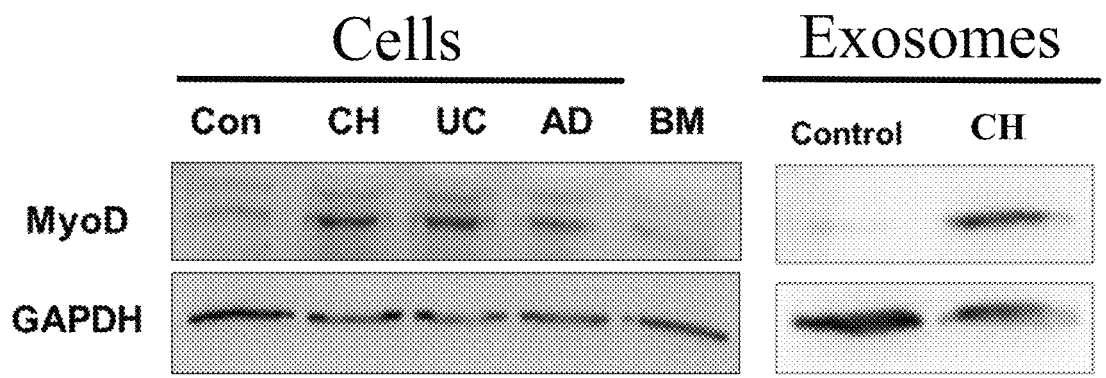

In vitro experiments with mouse cell line C2C12 and human muscle cells confirmed the expression changes caused by MSCs. Coculture in a trans-well plate of human muscle cells with MSCs showed that only UC- and CH-MSCs increased utrophin expression (FIG. 1F). Exosomes from these cells did as well. Muscle cell differentiation was also increased by AD-, CH-, and UC-MSCS and their exosomes, as measured by the formation of myotubes, (FIG. 1G) and expression of myosin heavy chain 2 respectively (FIG. 1H). However, when muscle cells from DMD patients were cocultured with MSCs only CH- and UC-MSC increased the formation of myotubes (FIG. 1I). Coculture of human satellite cells with UC- and CH-MSC, and their exosomes, increased asymmetric division (MyoD expression), although BM-MSCs did not (FIG. 1J). And coculture with C2C12 mouse muscle cells, showed similar results (FIG. 1K).

Example 2: MSCs Increase the Efficacy of Muscle Cell Engraftment

MSCs do not express MHCII molecules on their cell surface and thus are well tolerated as transplant cells. Further, MSCs have an immunomodulatory effect on the transplantee that results in immunosuppression which further improves tolerance. It has been proposed that many muscular diseases, muscular dystrophies and muscle injury, could be treated with muscle cell replacement therapy, however, such therapies have proven difficult to achieve owing to rejection of the graft. It was thus tested whether MSCs (CH and UC), when included in the graft, could decrease rejection and increase the engraftment of foreign cells. Generally, and throughout the following experiments, CH or UC MSCs were always used as they showed the greatest therapeutic and myogenic potential. Other areas of the placenta besides chorionic and amniotic tissues were examined, such as the placental villi, but no region showed the therapeutic potential that chorion did.

Figure 2:
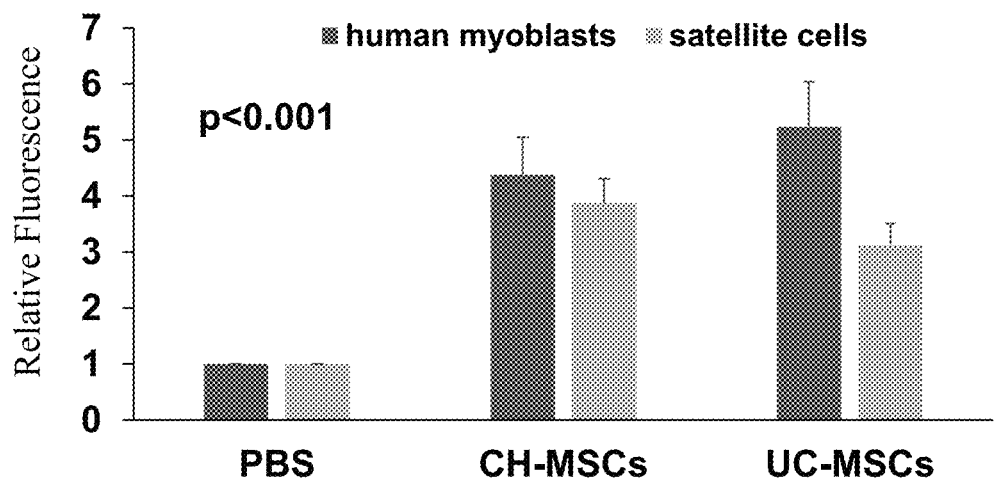
FIG. 2: MSCs increase the efficacy of muscle cell engraftment A bar chart showing relative fluorescence from transplanted human myoblasts or satellite cells 2 weeks after transplant. Cells were transplanted alone, or co-transplanted with MSCs.

MSCs were co-transplanted with human muscle cells labelled with a fluorescent red cell tracker into the tibialis anterior (TA) muscle of wild-type mice. After 2 weeks, the level of red fluorescence in the muscle was measured by microscopy, and both myoblast engraftment and satellite cell engraftment was examined. As compared to transplant without any MSCs, both UC- and CH-MSCs significantly increased the engraftment of myoblasts and satellite cells (FIG. 2). It was observed that UC-MSC co-transplant resulted in a better engraftment of myoblasts, while CH-MSC co-transplant resulted in a better engraftment of satellite cells, although the differences were not statistically significant. Similar results were observed 4 weeks after transplant as well.

Transplant of human astrocytes and neural stem cells (NSCs) was also tested. UC-MSCs or CH-MSCs were co-transplanted intrathecally with fluorescent red labeled cells and red fluorescence in the spinal cord was measured after 2 weeks and after 4 weeks in separate experiments. The level of red fluorescent after transplant of astrocytes was 4.55 (±0.67) with UC-MSCs and 3.89 (±0.54) with CH-MSCs and similar results were found for transplant of NSCs (control fluorescence set to 1). These experiments were repeated in MDX mice as well as a rat model for Amyotrophic Lateral Sclerosis (ALS) and in all cases co-transplantation with MSCs was found to improve muscle cell engraftment.

Example 3: MSCs Primed for Muscle Differentiation

Figure 3:
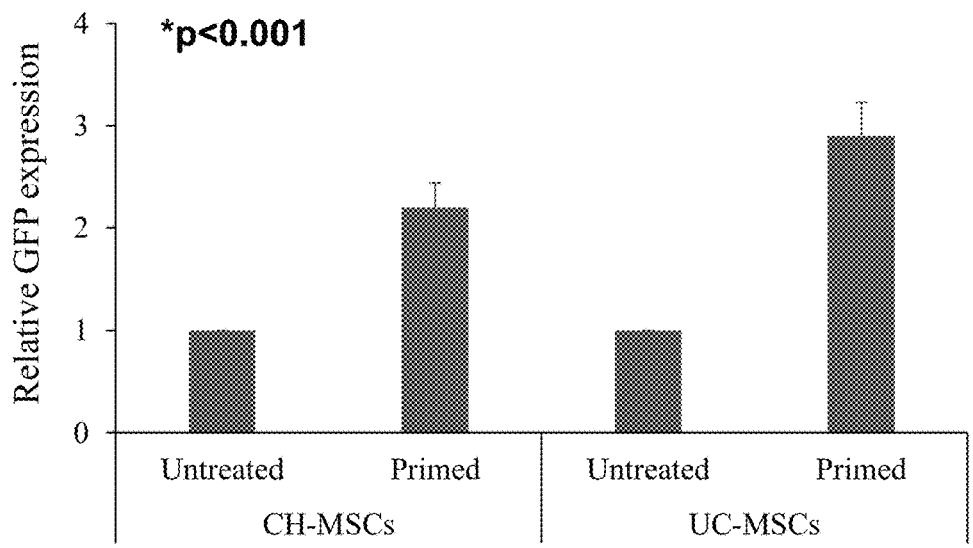
FIG. 3: Primed MSCs express MyoD A bar chart showing MyoD-GFP expression in primed MSCs.

In light of the ability of MSCs to induce muscle regeneration, reduce muscle fibrosis and increase engraftment via paracrine effects, a method of supplementing the therapeutic effect of MSCs was developed. This method, called "myogenic priming", increased the cell's paracrine effects on muscle cells on the one hand and promoted the MSC's own differentiation to muscle cells on the other. This priming increased the ability of MSCs to differentiate into satellite cells that undergo asymmetric division and to myoblasts that fuse with existing muscle fibers and deliver dystrophin to the cells. It was hypothesized that inducing MyoD expression in the cells would be one method of priming. This was tested by culturing CH- and UC-MSCs containing a MyoD-GFP reporter, in trans-well plates with human muscle cells (Protocol A). In this way, the extracellular vesicles and secreted factors from the muscle cells were able to contact the MSCs. A 3-day incubation resulting in a greater than 2-fold increase in MyoD expression as compared to control cells that had not be exposed to muscle cells (FIG. 3).

In addition to co-cultures with muscle cells, various methods were employed that would induced transient stem cell characteristics in MSCs to increase their muscle differentiation abilities in response to subsequent factors. Transfection of MSCs with a modified Nanog mRNA (such an mRNA is stable in the cytoplasm and can be immediately translated) prior to co-culture, increased myoD expression (Protocol B), as did a one day incubation of MSCs with 5-azacytidine (5-AZA) (Protocol C). This effect was enhanced when the two treatments were combined, with the transfected and co-cultured cells being incubated with 5-AZA. This led to a 5.7-fold increase in MyoD-GFP expression.

Incubation of the cells with a ROCK inhibitor (Y-27632) for 24 hours, followed by incubation in media with a pH of about 6 for 1 hour or exposure to hypoxia for 24 hours also induced a primed stem cell phenotype in MSCs (Protocol D). Additionally, incubation for 1-6 days with several small molecules such as STAT3, NF-KB activators, CHIR99021 (1-10 M), metformin (10 mg/ml), tranylcypromine (Parnate 1-10 µM), Gsk3 inhibitors, 3-deazaneplanocin A (1-10 µM), mTOR inhibitors (PP242, 1-10 µM), TGFβ inhibitors (RepSox), Thiazovivin (1-10 µM), A83-01 (0.5-1 µM), LiCl (5-10 mM), SB431542 (10 µM), and valproic acid (0.5-2.0 mM), rapamycin (1-10 Nm), ERK activators (resveratrol or fistein) or culture in low pH, hypoxia, and/or on low adherence culture plates with low levels of serum or human BSA with FGF or EGF (10 ng/ml) all primed the MSCs to a degree (Protocol E). These incubations were also performed after first transfecting the MSCs with the modified Nanog mRNA.

MSCs that were primed to express a transient stem cell phenotype were found to express SOX2, NANOG, OCT4 and KLF4 at levels higher than observed in untreated MSCs, as well as low levels of RTVP-1. These stemness markers were lowlier expressed when priming was performed by incubation with muscle extracellular vesicles. Due to the increase in stemness. it was tested whether the cells could differentiate into other cells of the mesenchymal lineage such as adipose, tendon or bone. Such differentiation was poor for all primed cells and impossible for cells primed by muscle extracellular vesicles.

To better understand the nature of the primed cells, various MSC, muscle and stemness markers were examined. All primed cells still expressed the MSC markers CD73, CD105, CD90, CD146 and CD44 and also did not express MHCII. They also expressed low to moderate levels of MyoD, MYF6, MYF5, ITGA7, osteprotegerin, irisin and Pax7. Though incubation with muscle extracellular vesicles caused the highest expression, the levels of these muscle markers were lower than what is observed in actual muscle cells. Cells primed with 5-AZA also expressed very high levels of VEGF and GDNF, trophic factors which are important for the survival of motor neurons and for the maintenance of the neuromuscular junction.

Example 4: Primed Cells Increase Regeneration and Decrease Fibrosis

Figure 4A:
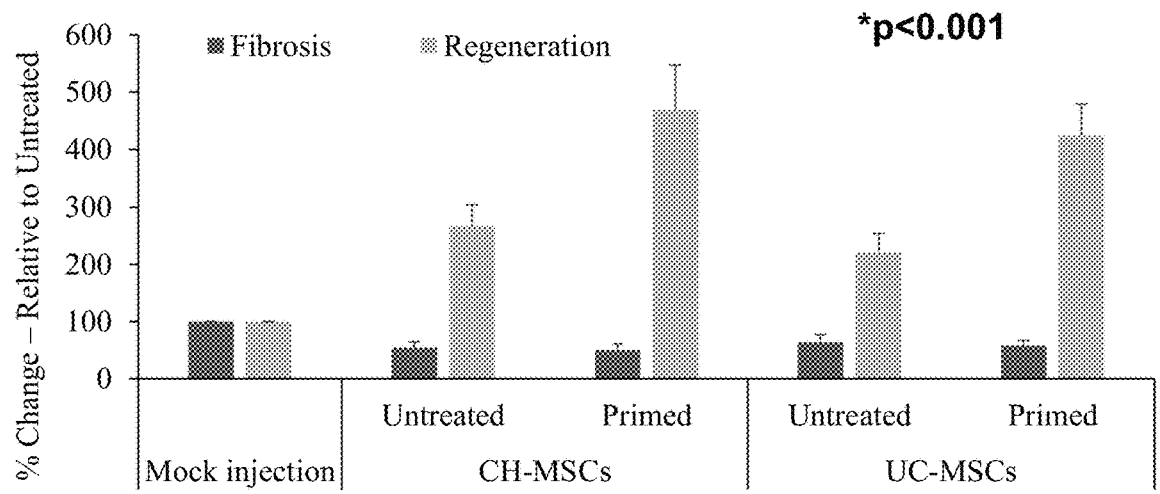
FIGS. 4A-4B: Primed cells increase regeneration and decrease fibrosis (FIG. 4A) A bar chart showing the percent change in expression of fibrosis marker Collagen I and regeneration marker NCAM in quadricep muscles of wild-type mice 4 weeks after injection of $1\times10^6$ unprimed and primed MSCs. Expression levels are measured relative to a control quadricep muscle which was mock injected.

As primed cells retain many of the characteristics of MSC, but also have begun down the path of muscle differentiation, how they compare to untreated MSC in their ability to increase regeneration and decrease fibrosis was tested. Untreated CH- and UC-MSCs were injected ($5 \times 10^5$ cells) into the left quadricep muscles of wild-type mice, while primed CH- and UC-MSCs were injected (5×105 cells differentiated by 5-AZA or muscle coculture) into the right. As previously observed MSCs derived from both tissues decreased fibrosis in the diaphragm and the heart (Collagen I expression) and increased regeneration in the injected muscle (NCAM expression), but notably, primed MSCs nearly doubled the level of regeneration, although the reduction in fibrosis was unchanged (FIG. 4A).

Figure 4B:
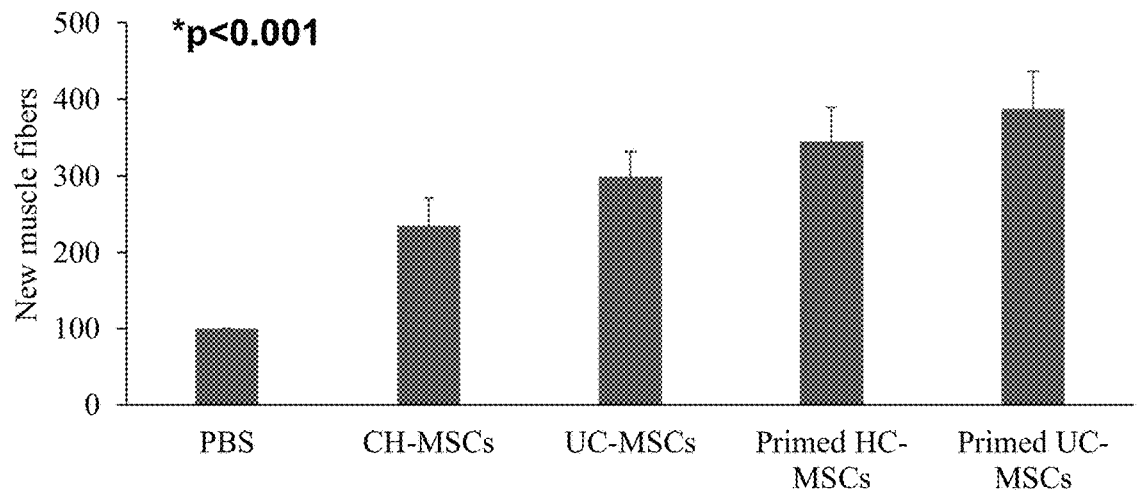

The ability of untreated and primed MSCs to induce new muscle formation in vivo was tested next. The TA muscle of wild-type mice was injected with either PBS, CH-MSCs, UC-MSCs, primed CH-MSCs or primed UC-MSCs (5×105 cells for all) and then treated with cardiotoxin to induce muscle injury. At seven days, the mice were sacrificed and newly generated muscle fibers in the gastrocnemius muscle were counted by noting MYH1 staining with centrally located nuclei. UC-MSCs more than doubled the number of new muscle cells, while CH-MSCs tripled it (FIG. 4B). Primed MSCs had an even stronger effect as primed UC-MSCs or CH-MSCs increased the number of new muscle cells by 344% and 387% respectfully.

Example 5: Selection of Tissue of Origin for Generation of MSC-Muscle Cell Hybrid Cells This data strongly suggests that the ability to fuse to a muscle syncytium as well as the MSC-like absence of MHCII and ability to decrease tissue rejection, are all useful in treating diseases that could benefit from muscle cell transplant/replacement. Thus, generating cells that combined both the paracrine effects of MSCs together with the ability to differentiate to supply normal satellite cells or myoblast is of great interest. Experimentation was performed to differentiate an MSC into such a hybrid cell.

MSCs from bone marrow (BM), adipose tissue (AD), umbilical cord (UC), chorionic placenta (CH) and amniotic placenta (AM) were all isolated and cultured according to standard MSC culturing conditions. The following differentiation protocol (Protocol 1) was then tested on all five samples. Cells were placed in media with a pH of about 6.0 for 1 hour. Following washing with PBS, the cells were returned to MSC media supplemented with a ROCK inhibitor (Y-27632) and cultured for 24 hours. Over the next 24 hours the cells were cultured in media supplemented with 5-Azacytidine (5-AZA). This was followed by incubation in media supplemented with HGF or PDGF, as well as infection of the cells with a lentivirus over-expressing PCAT1 and NEAT1.

Figure 5A:
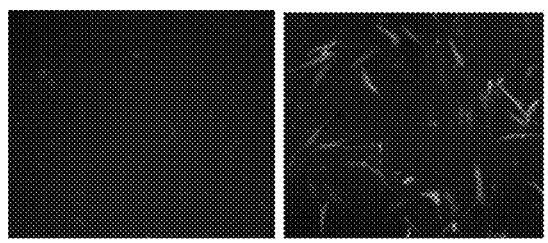
FIGS. 5A-5I: MSC-muscle cell hybrid cells express muscle markers and trophic factors (FIG. 5A) A micrograph showing MyoD expression in untreated MSCs and MSC differentiated to hybrid cells with Protocol 1.
Figure 5B:
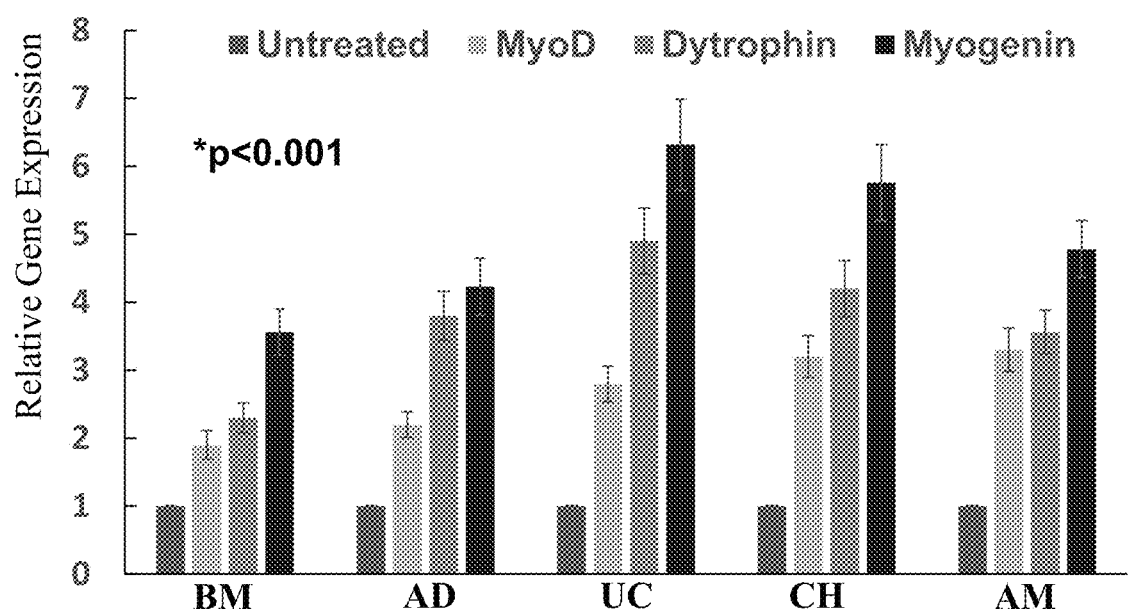
Figure 5C:
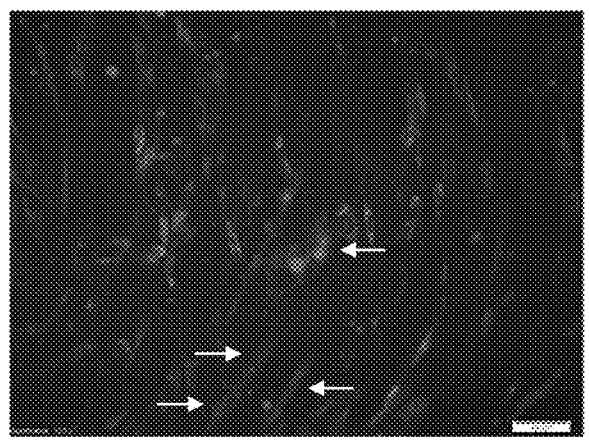

Following completion of this protocol, RNA was extracted from the cells and the expression of various MSC and muscle markers were examined by qRT-PCR. All treated MSCs were found to express increased levels of MyoD (FIG. 5A), Dystrophin and Myogenin as compared to untreated MSC from the same tissue, although MSCs from umbilical cord and chorion showed the highest expression (FIG. 5B). Adipose and amniotic MSCs were moderately inferior compared to UC and CH MSC, and bone marrow MSCs were found to be the poorest expressers of these muscle cell markers. Additionally, all treated cells were found to express muscle markers Myosin heavy chain (MYH), alpha 7 integrin (ITGA7), MYF6, MRF4, G-CSF, TALNEC2 and MEF2A, as well as high levels of IL-10. Interestingly, UC and CH MSCs also expressed osteoprotegerin, while BM and AD MSCs did not. Further, UC and CH MSCs expressed high levels of Irisin while the other MSCs only produced low expression. Importantly all hybrid cells showed the ability to fuse with human myoblasts when cultured together (FIG. 5C), showing that they possessed the ability to become part of a muscle syncytium and that they potentially can used for replacement cell therapy. Lastly, PAX7, a marker of satellite cells was expressed by all MSCs, however, CH-MSCs showed by far the highest expression, suggesting that they have a higher tendency to differentiate toward a satellite cell phenotype.

Importantly, following treatment the cells still did not express detectable levels of WICK and thus were still non-immunogenic. These cells therefore have a myogenic phenotype, but can still be employed as "off the shelf cells" for administration to human subjects. The cells still had not yet fully differentiated into muscle cells, as they still retained expression of CD73, CD105, CD146, and CD90, all markers present on MSCs and absent from muscle cells. The cells also expressed CD44 though at levels lower than in untreated cells. However, osteocalcin, PPARG3 and COL2A1, which are all highly expressed by MSCs, were all absent after completion of the differentiation protocol. Similarly, the expression of RTVP-1 was also reduced following differentiation. The treated cells were also tested for their ability to differentiate to other tissues of the mesenchymal lineage (bone, tendon, adipose). This ability was significantly decreased, once again attesting to the hybrid nature of the cells.

Figure 5D:
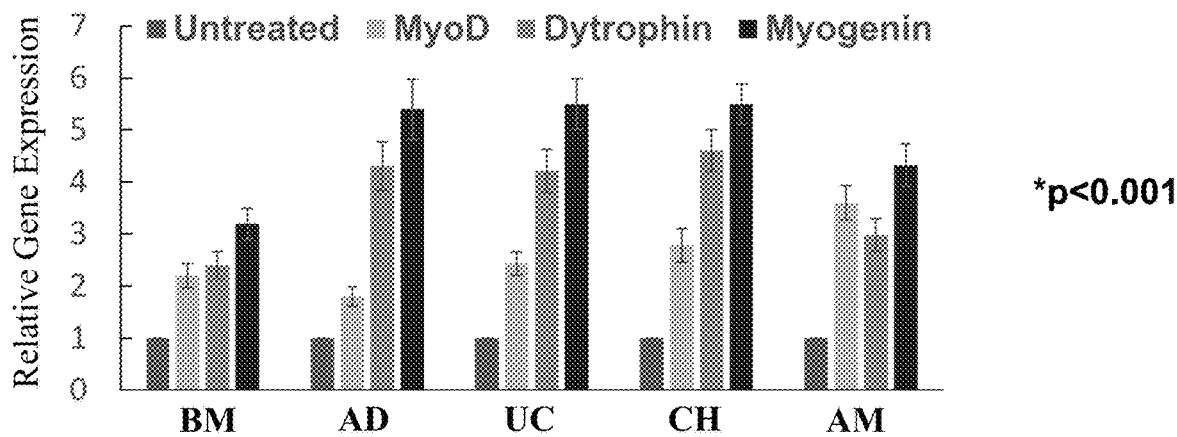

A second, similar, differentiation protocol (Protocol 2) was also examined. All five MSC types were again tested, and treatments with acidic medium, ROCK inhibitor, 5-AZA and HGF+PDGF were performed as before. However, instead of over expressing PCAT1 and NEAT1, the cells were transfected with GAS5 overexpressing plasmid as well as siRNAs against PTENP1. Once again, all five MSC types expressed MyoD, Dystrophin and Myogenin after completion of the treatment protocol, and once again a hierarchy was observed in which UC and CH were the best expressers, followed by AD and AM, and BM exerted the weakest effects (FIG. 5D). The general expression pattern observed after the first treatment was also present following the second protocol.

Figure 5E:
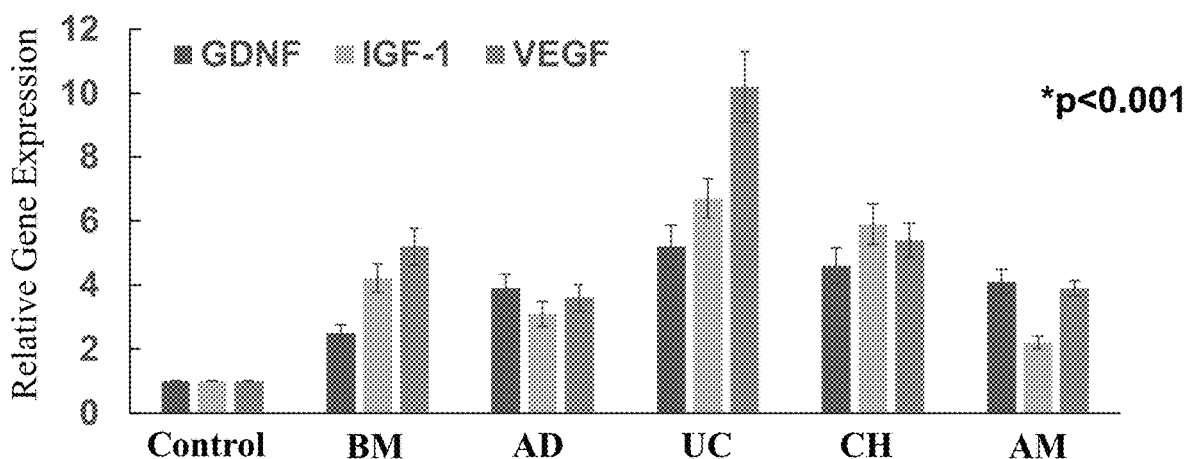

In addition to measuring markers of an induced muscle cell phenotype, the expression of trophic factors GDNF, VEGF, CNTF and IGF1 was also examined. MSCs are known to express many trophic factors that support neuronal function. Loss of such expression would be an undesirable side effect of differentiation toward a muscle cell phenotype. Strikingly, not only was the expression of these four trophic factors retained in the hybrid cells (and primed cells as well), but in fact expression of all four was greatly increased over what is observed in untreated MSCs (FIG. 5E). This increase was strongest in hybrid cells derived from UC-MSCs, with an over 10-fold increase in VEGF expression, an over 6-fold increase in IGF1 expression, an over 5-fold increase in GDNF expression and an over 4-fold increase in CNTF expression. CH-MSCs also yielded a greater than 4-fold increase for all 3 factors. Similar results were observed whether the first or second differentiation protocol was performed.

Example 6: Generation of MSC-Muscle Cell Hybrid Cells With TFs, miRs and lncRNAs As the most positive results were observed with MSCs derived from umbilical cord and chorion, these two sources of MSCs were used for all subsequent differentiations. A shortened third protocol (Protocol 3) was examined and was also found to produce MSC-muscle cell hybrid cells. The MSCs were cultured in normal MSC culturing conditions followed by supplementation of the media for 24 hours with 5-AZA. The cells were than grown in media supplemented with 2% horse serum and HGF and PDGF for 2 weeks. Similar results were observed with this shortened differentiation protocol. The following growth factors were tested both individually and in combination as replacements or in combination with HGF and PDGF: EGF, IGF1, PDGFAA, PDGFBB, and VEGF. All were found to produce hybrid cells. Additionally, the protocol could be halted by moving the treated MSCs to non-supplemented MSC media. Hybrid cells that were produced could thus be halted from further differentiation.

Figure 5F:
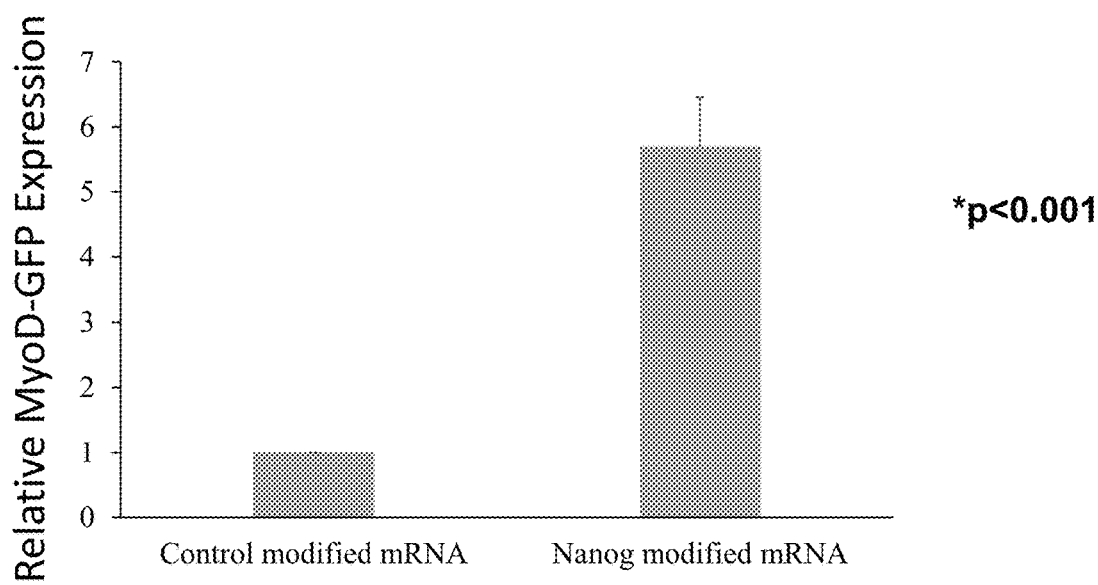

All three protocols were also performed with MSCs that had first undergone myogenic priming as described above. MSCs primed with a modified Nanog mRNA, and then treated with 5-AZA and PDGFBB as described in Protocol 3, for example, showed a nearly 6-fold increase in MyoD expression (FIG. 5F).

Direct expression of muscle transcription factors (TFs) also induced differentiation to a hybrid cell, especially when proceeded by myogenic priming or in combination with low pH, hypoxia, ROCK inhibitors or 5-AZA (Protocol 4). Lentivirus was used to express MYF5, PAX3, PAX7, dystrophin/microdystrophin, utrophin or a combination of MyoD+PAX3, MyoD+PAX7, or MyoD+MYF5 in both untreated and primed UC- and CH-MSCs. Expression profiles similar to those observed for the three previously described protocols were found using this method as well.

The TFs were also introduced into MSCs using lentivirus or AAV vectors containing a modified estrogen receptors responsive to tamoxifen and 4-hydroxytamoxifen. This allows the induction of the TFs in vivo at specific and optimal time points, taking first advantage of the paracrine effects of the MSCs and subsequently their replacement abilities. Since tamoxifen was reported to exert therapeutic effects in DMD, this approach can be doubly beneficial. The tamoxifen-inducible construct was tested, and its ability to induce specific TF expression in MSCs and induce myogenic differentiation in response to tamoxifen, was confirmed.

Non-coding RNAs have been implicated in the differentiation of various cells. To identify potential non-coding RNAs that play a role in the induction of myogenic differentiation, miRNA and lncRNA arrays comparing human muscle cells and MSCs were performed. MSCs were also differentiated to muscle cells using MyoD overexpression, and clusters of miRNAs and lncRNAs that are common to the muscle cells and the differentiated MSCs but different in the unmodified MSCs were identified. Alteration of expression of these miRNAs and lncRNAs upon differentiation of these MSCs to muscle cells was verified by rt-PCR.

Figure 5G:
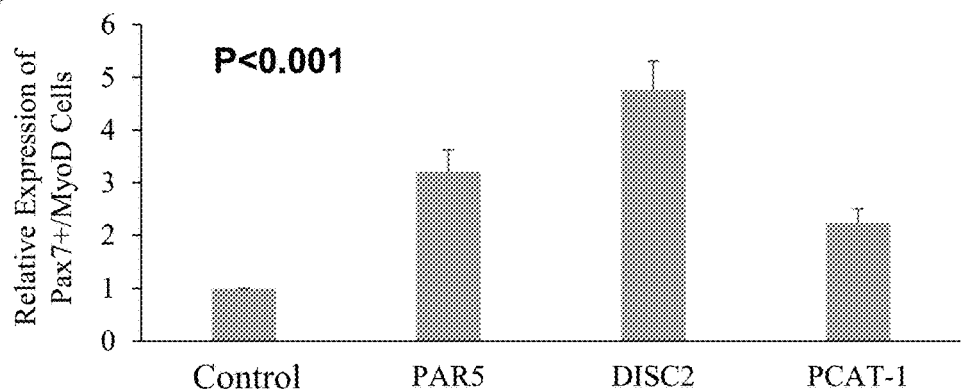
Figure 5H:
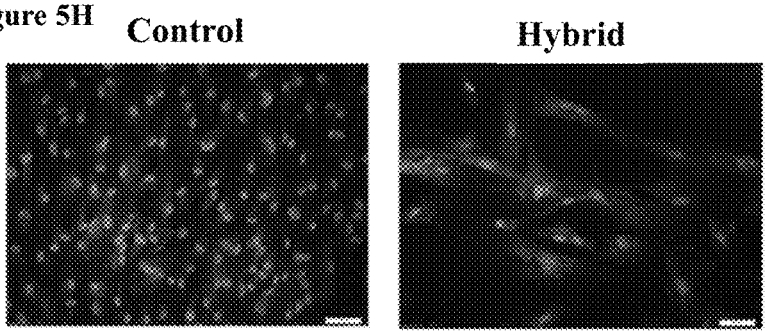

Differentiation was then carried out in MSCs as follows (Protocol 5): MSCs were incubated for 1 hour in acidic medium pH=5-6, followed by a 24-hour incubation with a ROCK inhibitor or 5-AZA, followed by introducing lncRNAs into the cell. To produce cells expressing satellite characteristics the following lncRNAs were used: BIL, PAR5, BIC, DISC2, GAS5DLG2AS, 7SK, Y1, LINCRNA, PCAT-1 SFMBT2, Y4 and SCA8. Hybrid cells produced by this method were confirmed to be double positive for MyoD and PAX7, indicating that they are fully functional as satellite cells and capable of asymmetric division (FIG. 5G). For the induction of more differentiated satellite cells and myoblasts, introduction of the following additional lncRNAs can be applied: MALAT1, MEG3, NEAT1, EGO, GAS5, KRASP1, LOC28519, BC200, and H19. Silencing of ANRIL, PTENP1 and aHIF also induced myogenic differentiation. Specifically, transfection of MSCs with the long lncRNAs listed above in combination with siRNAs against ANRIL, PTENP1 or aHIF, alone, or in combination, changed the morphological appearance of the cells (FIG. 5H) and the expression of specific muscle proteins (e.g. PAX7 and myoD expression in satellite cells and MyoD, myogenin, myosin heavy chain and dystrophin for more differentiated myogenic cells).

Figure 5I:
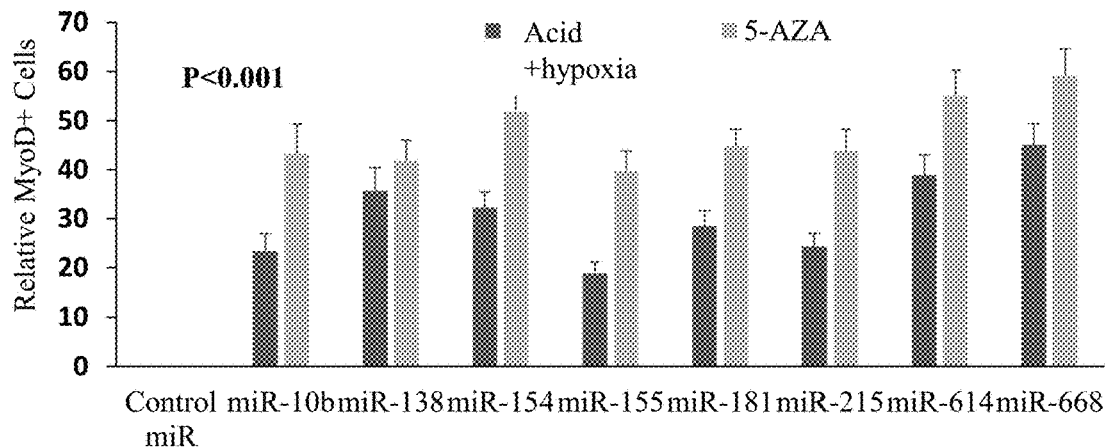

Differentiation was also carried out using the identified miRs (Protocol 6). The following miRs were all found to be altered upon MSC differentiation to muscle cell: miR-10b, miR-22, miR-122, miR-125a, miR-140-5p, miR-143, miR-145, miR-146a, miR-148b, miR-150, miR-155, miR-181b, miR-215, miR-296, miR-330, miR-370, miR-429, miR-520, miR-524, miR-543, miR-550, miR-561, miR-564, miR-582, miR-583, miR-587, miR-613, miR-614, miR-629, miR-634, miR-645, miR-646, miR-649, miR-661, miR-662, miR-663, miR-665, miR-668, miR-671, miR-887, miR-1183, miR-1224, miR-1225, miR-1228, miR-1234, miR-1246, miR-1247, miR-1257, miR-1258, miR-1268, miR-1269, miR-1289, miR-1287, miR-1909, miR-1911, miR-759, miR-3150, miR-3174, miR-3180, miR-3191, miR-3197, miR-4292, miR-2115 and miR 4312, miR-92, 93 and miR-99. MSCs were first myogenically primed by either incubation for 1 hour in acidic medium pH=5-6, followed by a 24-hour in hypoxia or by incubation for 24 hours with 5-AZA. Various miRs (miR-10b, miR-138, miR-154, miR-155, miR-181, miR-215, miR-614, and miR-668) were then introduced into the cell by transfection and MyoD expression was monitored (FIG. 5I).

Figure 6A:
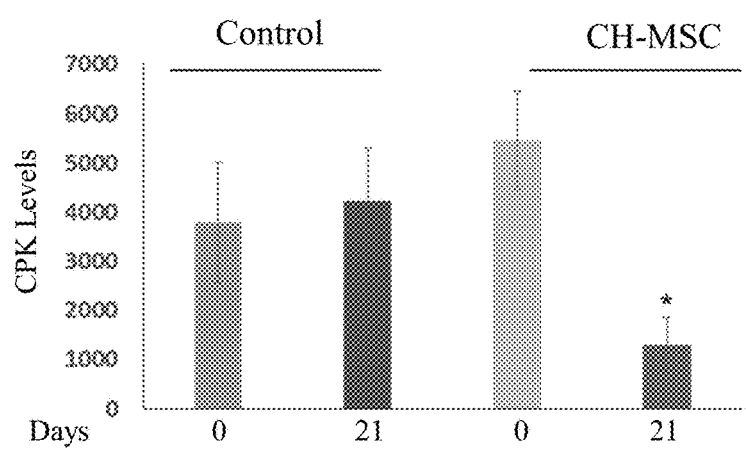
FIGS. 6A-6E: Use of CH-MSCs, primed MSCs or MSC-muscle cell hybrid cells to treat DMD (FIG. 6A) A bar chart showing creatine kinase (CPK) levels in mdx mice quadriceps muscles 3 weeks after control mock injection and injection with unmodified CH-MSCs.
Figure 6B:
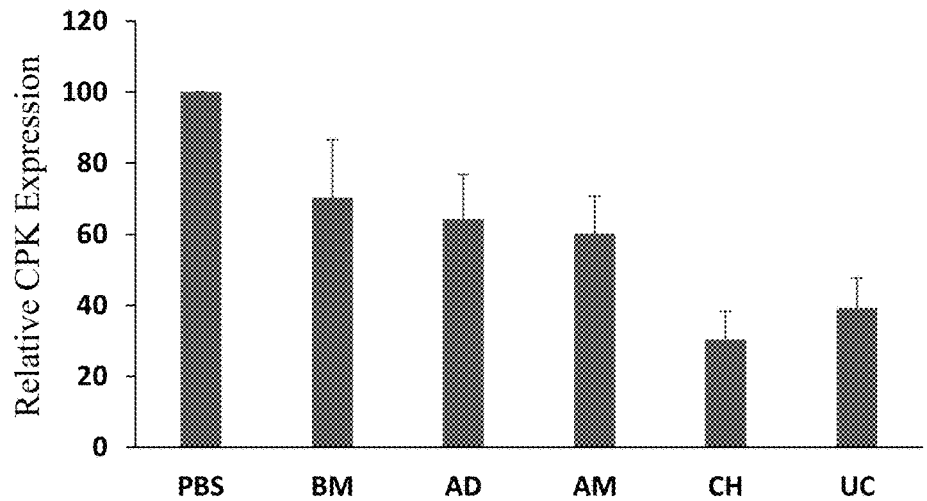

Example 7: Use of MSCs, Primed MSCs and MSC-Muscle Cell Hybrid Cells to Treat DMD Based on the above data, it was theorized that untreated MSCs, primed MSCs and hybrid cells could all be used as a therapeutic for treating Duchenne's Muscular Dystrophy (DMD). Mdx mice were used as a DMD model and creatine kinase (CPK) levels were measured to assess the efficacy of the therapy. Mice were injected in one quadricep muscle with unmodified CH-MSCs and mock injection was performed in the other quadricep. CPK levels were measured after 3 weeks, and untreated CH-MSCs decreased CPK levels by nearly 75% (FIG. 6A). The same experiment was repeated with MSCs derived from BM, AD, AM, CH and UC. MSCs derived from BM, AD and AM decreased CPK expression by 30-40%, UC-MSC decreased it by 60% and CH-MSCs once again caused a decrease of greater than 70% (FIG. 6B).

Figure 6C:
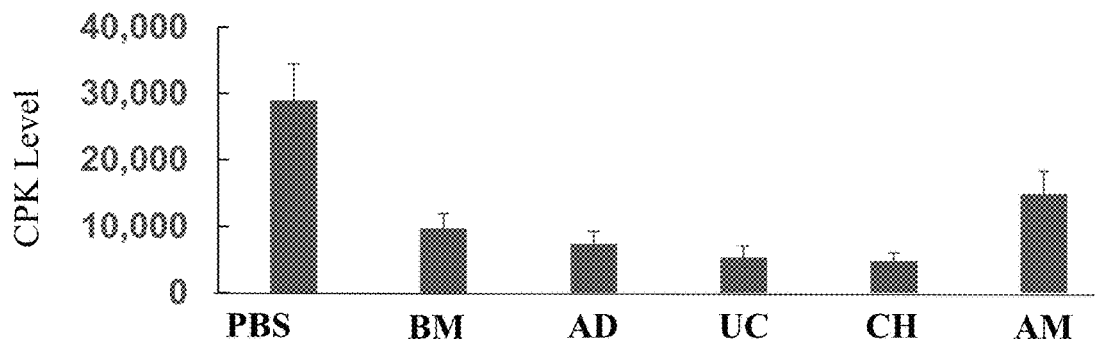

In order to test the efficacy of hybrid cells as compared to untreated MSCs, mdx mice were injected with PBS in one quadricep and in the other quadricep muscle hybrid cells derived from the same MSC source by protocol 1 were injected. All five sets of hybrid cells significantly decreased CPK levels in the quadricep after 3 weeks, with UC and CH derived cells again showing the greatest effect (Figure. 6C). Hybrid cells produced by protocol 2 had the same effect.

Figure 6D:
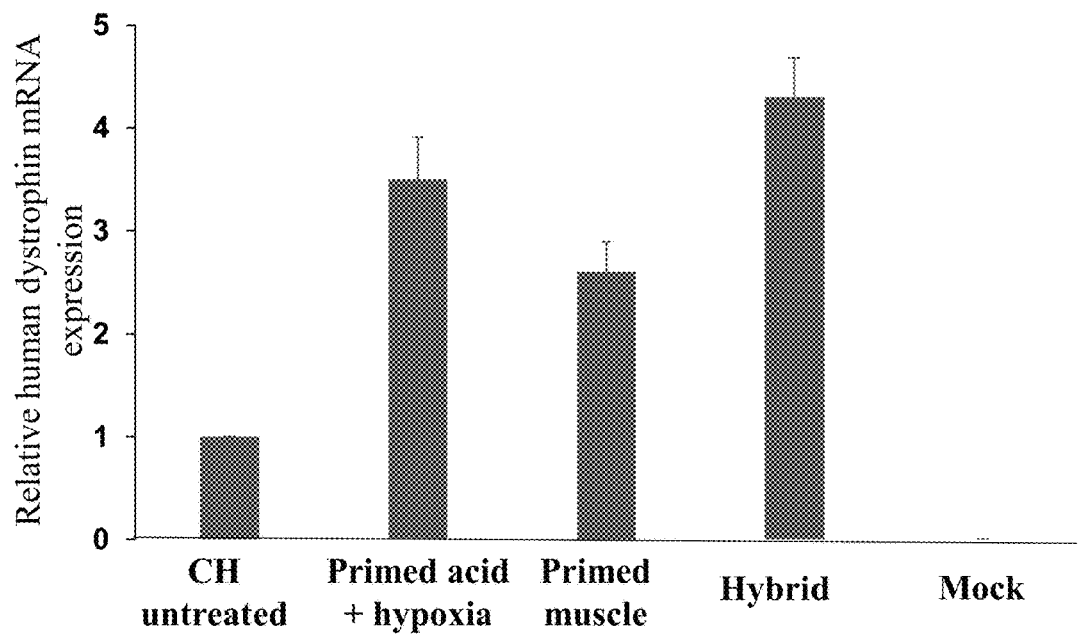

Primed MSCs were also tested. Once again, mdx mice were injected in one quadricep with untreated CH-MSCs, which as described above exert a therapeutic effect, and in the other with CH-MSCs primed by acidic media and ROCK inhibitors, CH-MSCs primed by coculture with muscle cells, or hybrid cells from CH-MSC produced by Protocol 3. All three modified cells produced an increased therapeutic effect as measured by the expression of human dystrophin in the mouse quadricep after 3 weeks (FIG. 6D). Human dystrophin was measured by qRT-PCR with primers unique for the human protein, thus entire increase in dystrophin measured was from the injected cells.

Figure 6E:
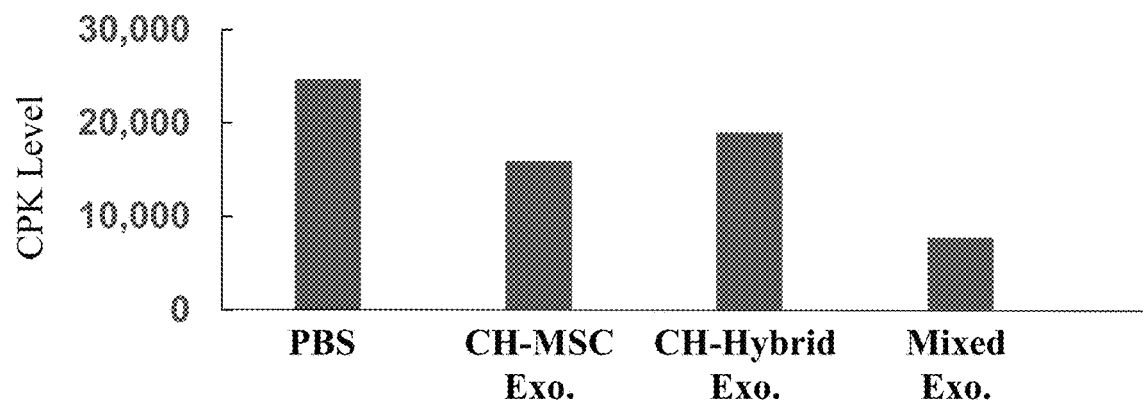

MSCs are known to secrete large numbers of extracellular vesicles and specifically exosomes, and it is known that these vesicles partially mediate MSCs' paracrine effects. In order to test if the extracellular vesicles of the hybrid cells also were partially responsible for the hybrid cell's therapeutic effect, the exosomes from $5 \times 10^5$ untreated or differentiated CH-MSC were injected into the quadriceps of MDX mice and CPK levels were measured. As seen in FIG. 6E both sets of exosomes reduced CPK levels, however the exosomes of untreated CH-MSC had a greater effect than exosomes from hybrid cells. Interestingly, a mix of exosomes from untreated CH-MSCs and hybrid cells had by far the greatest therapeutic effect.

Example 8: Use of MSC-Muscle Cell Hybrid Cells to Treat ALS

Figure 7A:
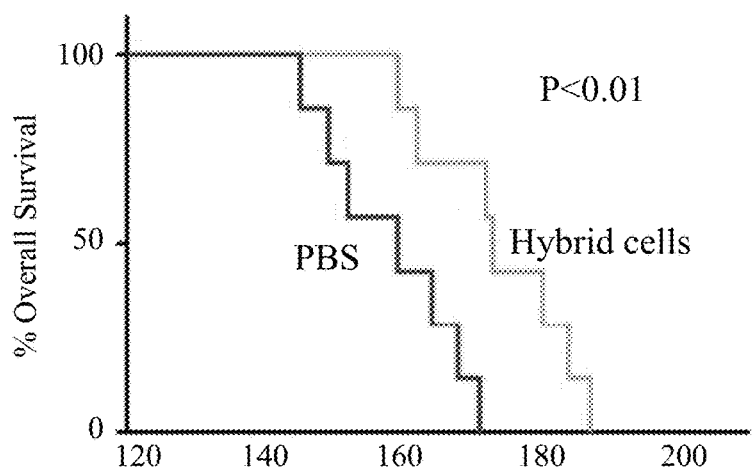
FIGS. 7A-7E: Use of MSC-muscle cell hybrid cells to treat ALS (FIG. 7A) A Kaplan-Meier survival plot of pre-symptomatic SOD rats injected intramuscularly with PBS or hybrid cells. Rats were sacrificed when no longer able to regain their upright position within 30 seconds after being placed on their backs.

Amyotrophic Lateral Sclerosis (ALS) is a motor neuron disease, but also involves gradually worsening weakness due to muscle loss. It was hypothesized that MSC-muscle cell hybrid cells might be effective in slowing the progression of muscular symptoms in ALS. To test this, hybrid cells derived from CH-MSCs using Protocol 1 were injected intramuscularly (IM) into the quadricep of pre-symptomatic SOD1G93A rats and the animals were monitored daily for symptom development. Specifically, rats were sacrificed when they could no longer regain their upright position within 30 seconds after being placed on their backs. Administration of hybrid cells as compared to PBS significantly increased the survival of the SOD mice, or to put it another way, hybrid cells significantly delayed the onset of ALS symptoms (FIG. 7A).

Figure 7B:
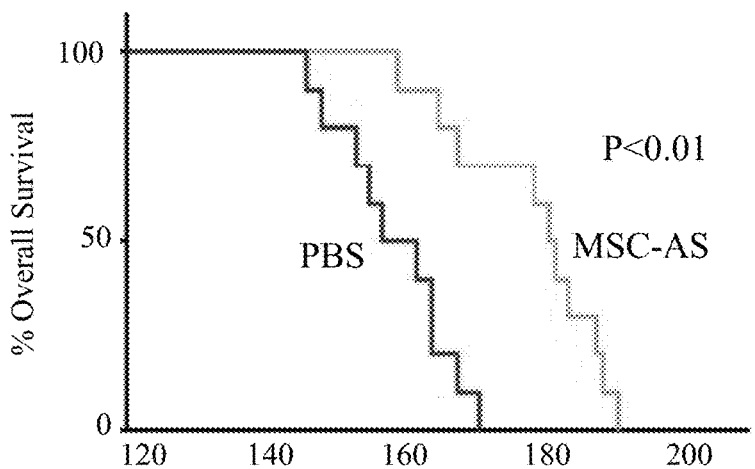

As ALS is a neuronal disease the same experiment was undertaken with MSCs that had been differentiated to an astrocyte phenotype (see US Application US20150037298, herein incorporated by reference). Administration of MSC-astrocytes intrathecally (IT) had a similar effect, and also significantly delayed the onset of ALS symptoms (FIG. 7B). These experiments were also repeated with injections of cells after the onset of symptoms, but before rats lost the ability to upright themselves. Similar, but reduced, effects were observed both with hybrid cells and MSC-astrocytes as compared to when injections were performed in pre-symptomatic rats.

Figure 7C:
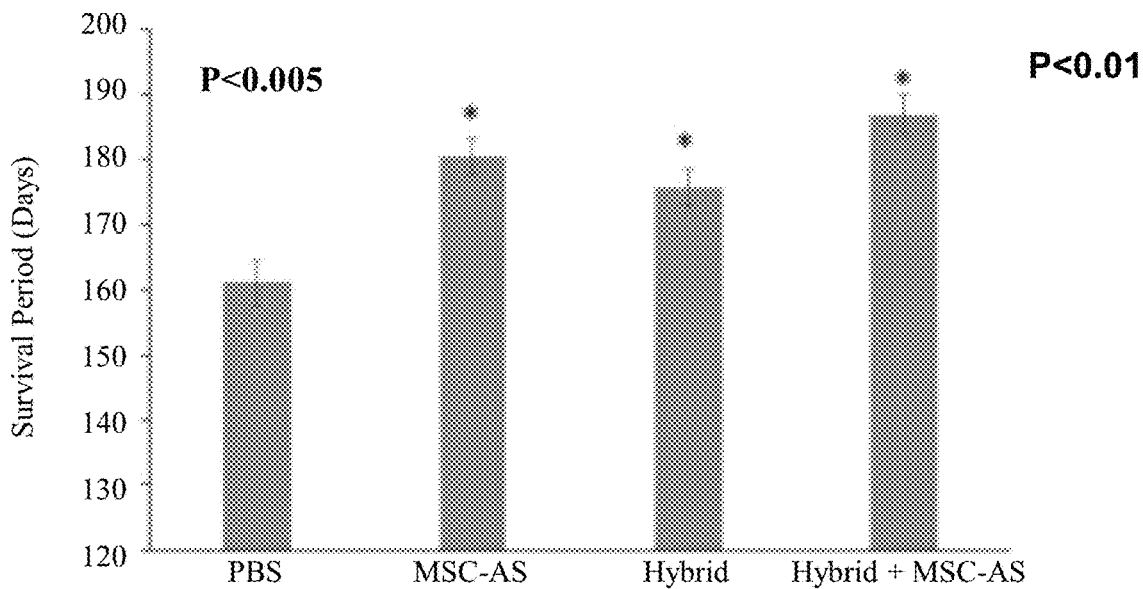

As both hybrid cells and MSC-astrocytes had a positive therapeutic effect, and as they were likely to affect different cellular targets, a combined therapy was investigated. Pre-symptomatic rats received both hybrid cells by IM administration and MSC-astrocytes by IT administration. A synergistic effect was observed, as the combination therapy increased survival (delayed the onset of symptoms) by a statistically significant amount as compared to either monotherapy (FIG. 7C).

Figure 7D:
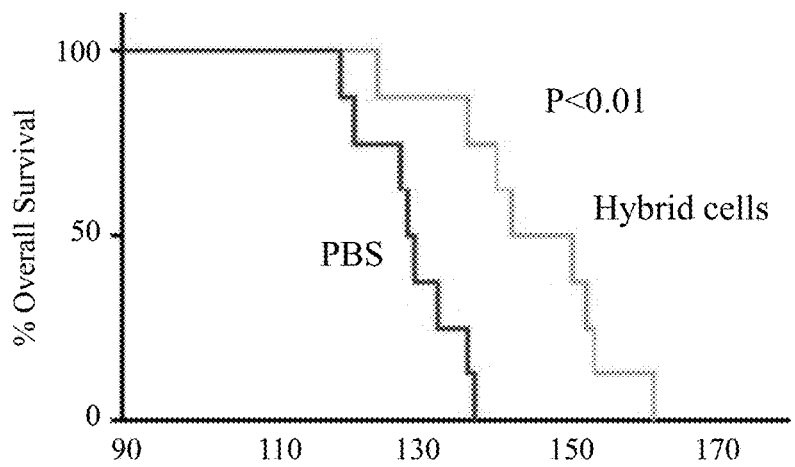
Figure 7E:
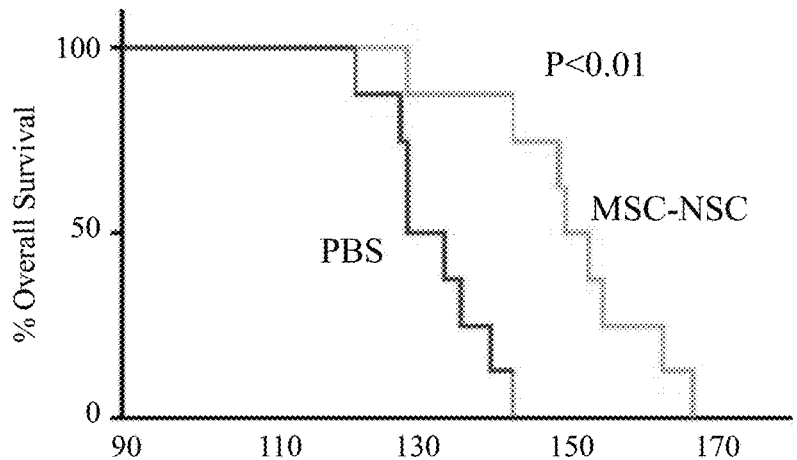

Multiple methods of testing for the onset of ALS symptoms exist, and so the experiments were repeated, but disease onset was determined by analyzing the ability of the rats to remain on a Rotarod for 10 minutes. By this measure as well, hybrid cells significantly delayed the onset of ALS symptoms (FIG. 7D). Intrathecal administration of MSCs differentiated into Neuronal Stem Cells (NSCs, see US Application US20150037299, herein incorporated by reference) also produced similar positive results (FIG. 7E). And once again, a combination therapy consisting of IM hybrid cells and IV MSC-NSCs produced a synergistic effect and increased the delay in ALS symptom onset.

Example 9: Use of MSCs and Their Exosomes to Treat Cachexia

Figure 8:
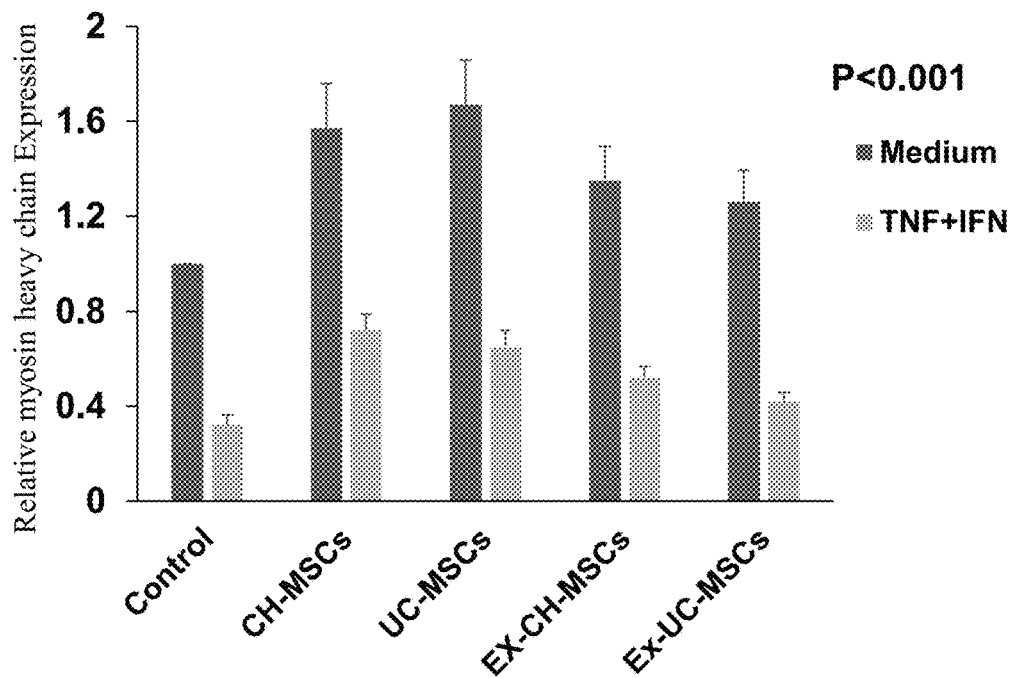
FIG. 8: Use of MSCs and their exosomes to treat cachexia A bar chart showing relative myosin heavy chain expression in muscle cells cocultured with CH- and UC-MSCs and their exosomes after mock treatment with media and treatment with TNFα and IFNγ.

Cachexia, weakness or wasting of the muscles of the body due to chronic illness or cancer, was another muscle malady for which the use of MSCs was investigated. Human muscle cells were cocultured in trans-well plates with CH- or UC-MSC or their exosomes. As expected, both the cells and the exosomes increased expression of myosin heavy chain (FIG. 8) indicating increased muscle growth. Treatment of the cells with proinflammatory TNFα and IFNγ mimicked cachexia and reduced myosin heavy chain expression by over 60% in control muscle cells. A significant inhibition of this effect was observed in muscle cells cocultured with UC- and CH-MSCs, albeit to a different degree Addition of exosomes also improved myosin heavy chain expression, but not to the levels of MSCs themselves (FIG. 8).

A second model of cachexia was also employed. Human immortalized muscle cells were incubated with exosomes from human cell lines associated with cachexia (such as primary lung tumor cells). The cachexia exosomes induced muscle cell death, inhibited differentiation and decreases myosin heavy chain expression in the immortalized cells. However, coculture with UC- and CH-MSCs or their exosomes abrogated these cachexic effects, as decreased cell death, and increased differentiation and myosin heavy chain expression were observed.

Example 10: Use of MSCs as a Therapeutic Delivery System

Several potentially promising therapeutics exist for muscle, motor neuron, and peripheral neuron disease and injury. However, frequently there is difficulty in delivering the therapeutic directly and specifically to the injured or diseased area. Due to the homing ability of MSCs, along with their large repertoire of secreted vesicles it was hypothesized that MSCs might serve as ideal delivery agents to muscles and neurons.

Figure 9A:
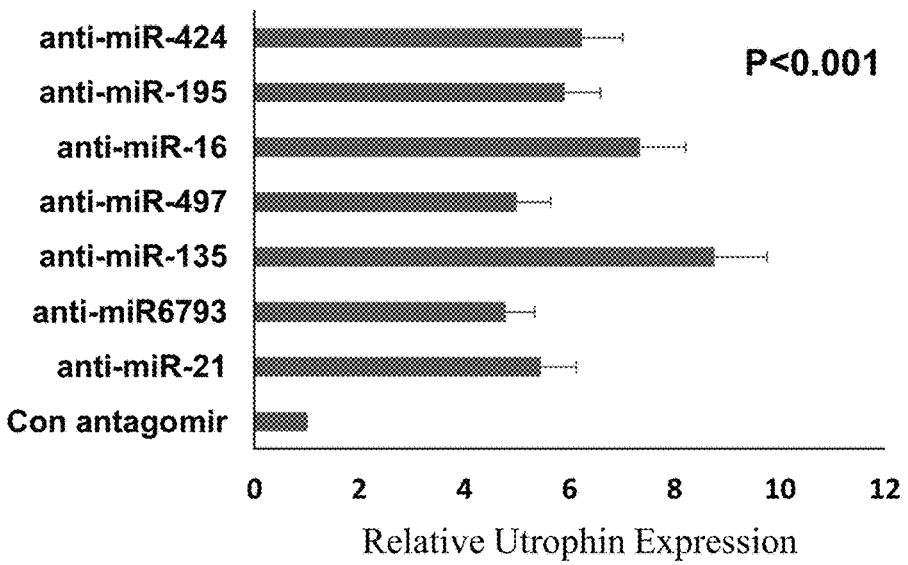
FIGS. 9A-9E: Use of MSCs as a therapeutic delivery system (FIG. 9A) A bar chart showing relative Utrophin mRNA expression in myoblasts following incubation with exosomes from MSCs loaded with the listed antagomirs.

To test this hypothesis exosomes derived from unmodified CH- and UC-MSCs were loaded with antagomirs against several microRNAs (miRs) known to reduce utrophin expression (anti-miR-424, 195, 16, 497, 135, 6793, and 21), and incubated with human myoblasts. Incubation with these exosomes greatly increased utrophin mRNA expression in the myoblasts, indicating that the exosomes had successfully transferred the antagomirs to the myoblasts (FIG. 9A).

Figure 9B:
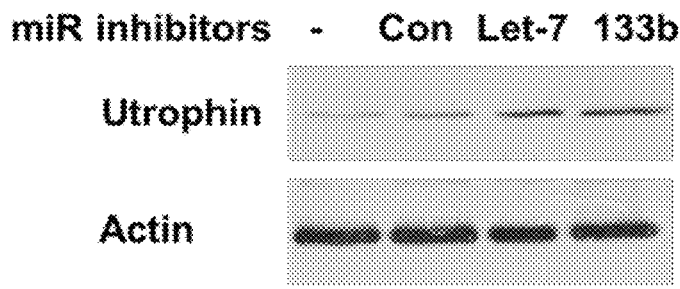
Figure 9C:
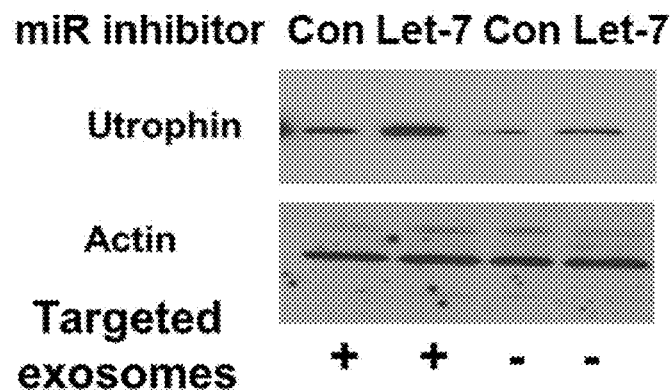
Figure 9D:
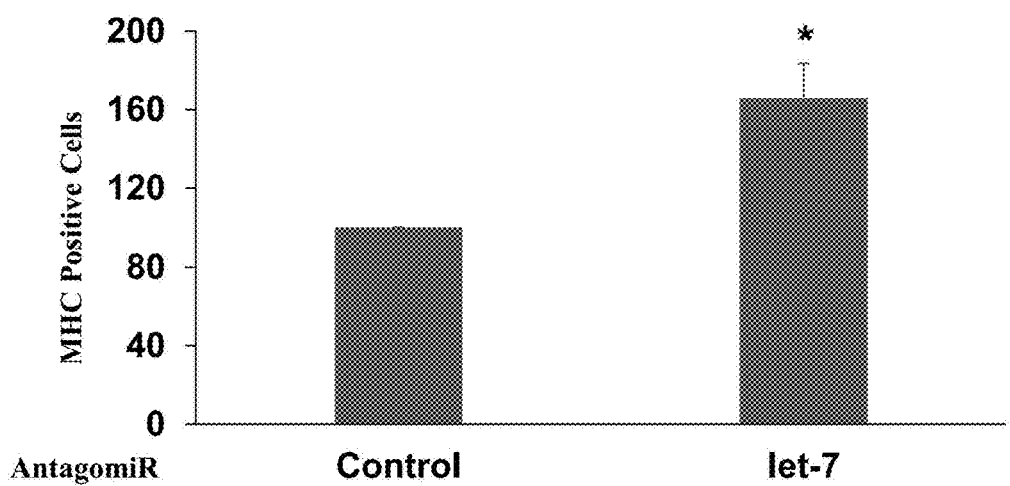

Similarly, CH-MSCs transfected with a let-7 antagomir or a miR-133b antagomir transferred the antagomir to muscle cells in vitro resulting in increased utrophin protein expression (FIG. 9B). Exosomes from these cells also successfully increased utrophin protein expression in vitro (FIG. 9C). Next, exosomes targeted to muscle cells by a M-cadherin epitope on the exosome surface were administered to a mixed muscle cell/astrocyte culture. The targeted-exosomes containing anti-let-7 increased utrophin expression in 55-68% of the astrocyte cells in the culture, but also did so in 85-92% of muscle cells in the culture (FIG. 9C, muscle cell lysate shown). This indicated that not only do the exosomes transfer antagomirs, but that muscle targeting moieties on the exosomes (or MSCs) will increase the effectiveness of the transfer. Let-7 is also known to decrease myosin heavy chain expression and thus inhibit muscle regeneration. The let-7 antagomir also significantly increased myosin heavy chain expression (FIG. 9D) and thus had a double therapeutic benefit.

Delivery of dystrophin protein is also a much-investigated therapeutic avenue, however, recombinant dystrophin induces a robust immunogenic response and, as yet, no effective delivery system has been discovered. As MSCs have immunosuppressive abilities, unmodified CH-MSCs were infected with viral vectors expressing dystrophin and microdystrophin in hopes that they would allow for dystrophin expression without an immune response. To further augment the effects of these plasmids, MSCs expressing an antagomir to miR-214, a miR that targets dystrophin, were also employed. The combined effect of the dystrophin plasmid and anti-miR-214, were striking with dystrophin expression increased by about 4.5-fold. Importantly, this treatment also increased utrophin expression. Thus, anti-miR-214 delivery also has a double therapeutic benefit as it increases both dystrophin and utrophin expression.

Figure 9E:
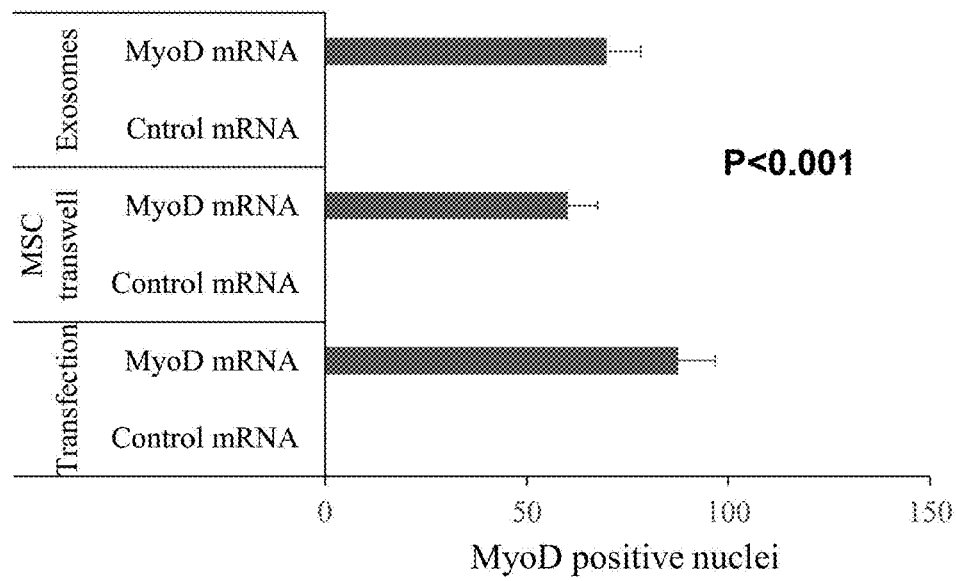

The ability of exosomes and MSC to deliver therapeutics was further tested by loading MSCs and exosomes with a modified myoD mRNA. Such an mRNA upon entering the cytoplasm of a cell can be immediately translated into protein. Direct addition of myoD loaded exosomes to myoblasts as well as coculture of loaded MSCs and myoblasts in a trans-well plate resulted in robust myoD expression as measured by the number of myoD positive nuclei (FIG. 9E). Direct transfection of cells with the modified myoD mRNA was used as a positive control, and indeed transmission of the mRNA by exosome or coculture was nearly as effective as direct administration by transfection. Thus, MSCs and their exosomes can effectively deliver modified mRNAs, similar to other RNA molecules.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of treating a muscular dystrophy, the method comprising administering to the subject a pharmaceutical composition comprising a therapeutically effective amount of chorionic placenta mesenchymal stem cells (MSCs), exosomes from said chorionic placenta MSCs or both.

2. The method of claim 1, wherein said MSCs are allogenic or autologous to said subject.

3. The method of claim 1, wherein said muscular dystrophy is Duchene's muscular dystrophy (DMD).

4. The method of claim 3, wherein the method decreases creatine kinase (CPK) levels in said subject.

5. The method of claim 1, wherein the method increases utrophin expression, decreases fibrosis, or both.

6. The method of claim 1, wherein the method increases dystrophin expression.

7. The method of claim 5, wherein said fibrosis occurs in the heart, diaphragm or both.

8. The method of claim 5, wherein said decrease in fibrosis comprises a decrease in collagen I expression.

9. The method of claim 1, wherein said method further decreases inflammation in said subject.

10. The method of claim 9, wherein said decreasing inflammation comprises decreasing expression of at least one proinflammatory cytokine.

11. A method of treating a muscular dystrophy, the method comprising administering to the subject a pharmaceutical composition comprising a therapeutically effective amount of chorionic placenta or umbilical cord MSCs, exosomes from said chorionic placenta or umbilical cord MSCs or both and administering a muscle cell to said subject.

12. The method of claim 11, wherein said muscle cell is administered at the same time as said pharmaceutical composition.

13. The method of claim 11, wherein said muscle cell is selected from a myoblast and a satellite cell.

14. A method of treating a muscular dystrophy, the method comprising administering to the subject a pharmaceutical composition comprising a therapeutically effective amount of chorionic placenta or umbilical cord MSCs, exosomes from said chorionic placenta or umbilical cord MSCs or both and administering any one of:
   a. an MSC transdifferentiated toward a muscle cell phenotype,
   b. an extracellular vesicle of said transdifferentiated MSC, and
   c. a combination thereof.

15. The method of claim 1, wherein said chorionic placenta MSCs, exosomes from said chorionic placenta MSCs or both comprise a muscle-targeting moiety.

16. The method of claim 15, wherein said muscle-targeting moiety is a M-cadherin epitope.

17. The method of claim 1, wherein said chorionic placenta MSCs, exosomes from said chorionic placenta MSCs or both, comprise at least one anti-muscular dystrophy therapeutic agent.

18. The method of claim 17, wherein said at least one agent is a RNA oligonucleotide that hybridizes to and inhibits a microRNA (miR) and said miR is selected from the group consisting of: miR-424, miR-195, miR-16, miR-497, miR-135, miR-6793, miR-21, let-7, miR-133b, and miR-214.

19. The method of claim 17, wherein said at least one agent is a nucleic acid molecule capable of inducing dystrophin or microdystrophin expression.

20. The method of claim 19, wherein said chorionic placenta MSCs, exosomes from said chorionic placenta MSCs or both, further comprise a RNA oligonucleotide that hybridizes to and inhibits miR-214.

* * * * *

SEQUENCE LISTING

```
<160> NUMBER OF SEQ ID NOS: 40

<210> SEQ ID NO 1
<211> LENGTH: 20
<212> TYPE: DNA
<213> ORGANISM: Homo sapien

<400> SEQUENCE: 1
atcagccaca tcgcccagca                                                    20

<210> SEQ ID NO 2
<211> LENGTH: 20
<212> TYPE: DNA
<213> ORGANISM: Homo sapien

<400> SEQUENCE: 2
cccagcagcc tcaaaatcct                                                    20

<210> SEQ ID NO 3
<211> LENGTH: 19
<212> TYPE: DNA
<213> ORGANISM: Homo sapiens

<400> SEQUENCE: 3
tgggttcggt ggtcaagtc                                                     19

<210> SEQ ID NO 4
<211> LENGTH: 19
<212> TYPE: DNA
<213> ORGANISM: Homo sapiens

<400> SEQUENCE: 4
cgctctggta gtgctggga                                                     19

<210> SEQ ID NO 5
<211> LENGTH: 20
<212> TYPE: DNA
<213> ORGANISM: Homo sapiens

<400> SEQUENCE: 5
tgctggaggt gtaatggacg                                                    20

<210> SEQ ID NO 6
<211> LENGTH: 20
<212> TYPE: DNA
<213> ORGANISM: Homo sapiens

<400> SEQUENCE: 6
caagcacaca aagatgggct                                                    20
```

-continued

```
<210> SEQ ID NO 7
<211> LENGTH: 20
<212> TYPE: DNA
<213> ORGANISM: Homo sapiens

<400> SEQUENCE: 7
ggtgcttgtt cctcagcctc                                              20

<210> SEQ ID NO 8
<211> LENGTH: 19
<212> TYPE: DNA
<213> ORGANISM: Homo sapiens

<400> SEQUENCE: 8
caggcagaag agcgtggtg                                               19

<210> SEQ ID NO 9
<211> LENGTH: 20
<212> TYPE: DNA
<213> ORGANISM: Homo sapiens

<400> SEQUENCE: 9
tctcattgtt tttaagccta                                              20

<210> SEQ ID NO 10
<211> LENGTH: 23
<212> TYPE: DNA
<213> ORGANISM: Homo sapiens

<400> SEQUENCE: 10
catctacgat gtcagtactt cca                                          23

<210> SEQ ID NO 11
<211> LENGTH: 20
<212> TYPE: DNA
<213> ORGANISM: Homo sapiens

<400> SEQUENCE: 11
gcgcttgaac atcatcagcc                                              20

<210> SEQ ID NO 12
<211> LENGTH: 17
<212> TYPE: DNA
<213> ORGANISM: Homo sapiens

<400> SEQUENCE: 12
ggaacgcgtg tgcgagt                                                 17

<210> SEQ ID NO 13
<211> LENGTH: 20
<212> TYPE: DNA
<213> ORGANISM: Mus musculus

<400> SEQUENCE: 13
tctcatcgta cctaagcctc                                              20

<210> SEQ ID NO 14
<211> LENGTH: 24
<212> TYPE: DNA
<213> ORGANISM: Mus musculus

<400> SEQUENCE: 14
cagtgccttg ttgacattgt tcag                                         24
```

<210> SEQ ID NO 15
<211> LENGTH: 22
<212> TYPE: DNA
<213> ORGANISM: Homo sapiens

<400> SEQUENCE: 15
tgaaagagat ggggaggaac ca                                              22

<210> SEQ ID NO 16
<211> LENGTH: 21
<212> TYPE: DNA
<213> ORGANISM: Homo sapiens

<400> SEQUENCE: 16
ggcagaagag ggcaatgaca c                                               21

<210> SEQ ID NO 17
<211> LENGTH: 23
<212> TYPE: DNA
<213> ORGANISM: Homo sapiens

<400> SEQUENCE: 17
ccagttttca cataatacac ggc                                             23

<210> SEQ ID NO 18
<211> LENGTH: 20
<212> TYPE: DNA
<213> ORGANISM: Homo sapiens

<400> SEQUENCE: 18
aagagcgtca aagccagaaa                                                 20

<210> SEQ ID NO 19
<211> LENGTH: 20
<212> TYPE: DNA
<213> ORGANISM: Homo sapiens

<400> SEQUENCE: 19
aaacatccag gtcaaccccc                                                 20

<210> SEQ ID NO 20
<211> LENGTH: 20
<212> TYPE: DNA
<213> ORGANISM: Homo sapiens

<400> SEQUENCE: 20
accactcgac tccacagtct                                                 20

<210> SEQ ID NO 21
<211> LENGTH: 20
<212> TYPE: DNA
<213> ORGANISM: Homo sapiens

<400> SEQUENCE: 21
acctcatccc tgtctattgc                                                 20

<210> SEQ ID NO 22
<211> LENGTH: 20
<212> TYPE: DNA
<213> ORGANISM: Homo sapiens

<400> SEQUENCE: 22

```
ctgttggctc cttgcttgtt                                               20

<210> SEQ ID NO 23
<211> LENGTH: 20
<212> TYPE: DNA
<213> ORGANISM: Homo sapiens

<400> SEQUENCE: 23
ctccacctga agaagattgt                                               20

<210> SEQ ID NO 24
<211> LENGTH: 20
<212> TYPE: DNA
<213> ORGANISM: Homo sapiens

<400> SEQUENCE: 24
aagatgtaac ctcctgaagt                                               20

<210> SEQ ID NO 25
<211> LENGTH: 20
<212> TYPE: DNA
<213> ORGANISM: Homo sapiens

<400> SEQUENCE: 25
attccccagc aactcttctt                                               20

<210> SEQ ID NO 26
<211> LENGTH: 20
<212> TYPE: DNA
<213> ORGANISM: Homo sapiens

<400> SEQUENCE: 26
tacagcaacc acttcccatt                                               20

<210> SEQ ID NO 27
<211> LENGTH: 20
<212> TYPE: DNA
<213> ORGANISM: Homo sapiens

<400> SEQUENCE: 27
gaacctgacc tcccactgaa                                               20

<210> SEQ ID NO 28
<211> LENGTH: 20
<212> TYPE: DNA
<213> ORGANISM: Homo sapiens

<400> SEQUENCE: 28
tcctgcctgc ttacgccaac                                               20

<210> SEQ ID NO 29
<211> LENGTH: 19
<212> TYPE: DNA
<213> ORGANISM: Homo sapiens

<400> SEQUENCE: 29
caaccaggag gagcgtgac                                                19

<210> SEQ ID NO 30
<211> LENGTH: 18
<212> TYPE: DNA
<213> ORGANISM: Homo sapiens

<400> SEQUENCE: 30
```

```
cagccgtgag cagatgat                                                 18

<210> SEQ ID NO 31
<211> LENGTH: 20
<212> TYPE: DNA
<213> ORGANISM: Homo sapiens

<400> SEQUENCE: 31
atgatacggg acgaacaggg                                               20

<210> SEQ ID NO 32
<211> LENGTH: 20
<212> TYPE: DNA
<213> ORGANISM: Homo sapiens

<400> SEQUENCE: 32
tgaacttgcc acttgcttga                                               20

<210> SEQ ID NO 33
<211> LENGTH: 20
<212> TYPE: DNA
<213> ORGANISM: Homo sapiens

<400> SEQUENCE: 33
cccacctcca actgctctga                                               20

<210> SEQ ID NO 34
<211> LENGTH: 20
<212> TYPE: DNA
<213> ORGANISM: Homo sapiens

<400> SEQUENCE: 34
caactggaga gagagaagcc                                               20

<210> SEQ ID NO 35
<211> LENGTH: 20
<212> TYPE: DNA
<213> ORGANISM: Homo sapiens

<400> SEQUENCE: 35
caccccacat cttctccatc                                               20

<210> SEQ ID NO 36
<211> LENGTH: 20
<212> TYPE: DNA
<213> ORGANISM: Homo sapiens

<400> SEQUENCE: 36
ccttcttctt ctccccagta                                               20

<210> SEQ ID NO 37
<211> LENGTH: 18
<212> TYPE: DNA
<213> ORGANISM: Homo sapiens

<400> SEQUENCE: 37
ccgcagccgc cttctatg                                                 18

<210> SEQ ID NO 38
<211> LENGTH: 18
<212> TYPE: DNA
<213> ORGANISM: Homo sapiens
```

```
<400> SEQUENCE: 38
acaccgccgc actcttcc                                                 18

<210> SEQ ID NO 39
<211> LENGTH: 20
<212> TYPE: DNA
<213> ORGANISM: Homo sapiens

<400> SEQUENCE: 39
tgataacggc taaggaagga                                               20

<210> SEQ ID NO 40
<211> LENGTH: 18
<212> TYPE: DNA
<213> ORGANISM: Homo sapiens

<400> SEQUENCE: 40
cacgatggaa gaaaggca                                                 18
```